(12) United States Patent
Yaghi et al.

(10) Patent No.: US 9,045,387 B2
(45) Date of Patent: Jun. 2, 2015

(54) OXIDATIVE HOMO-COUPLING REACTIONS OF ARYL BORONIC ACIDS USING A POROUS COPPER METAL-ORGANIC FRAMEWORK AS A HIGHLY EFFICIENT HETEROGENEOUS CATALYST

(75) Inventors: Omar M. Yaghi, Los Angeles, CA (US); Alexander U. Czaja, Dirmstein (DE); Bo Wang, Beijing (CN); Zheng Lu, Los Angeles, CA (US)

(73) Assignees: The Regents of the University of California, Oakland, CA (US); BASF SE, Ludwigshafen (DE)

( * ) Notice: Subject to any disclaimer, the term of this patent is extended or adjusted under 35 U.S.C. 154(b) by 0 days.

(21) Appl. No.: 13/387,598

(22) PCT Filed: Jul. 27, 2010

(86) PCT No.: PCT/US2010/043373
§ 371 (c)(1),
(2), (4) Date: Jan. 27, 2012

(87) PCT Pub. No.: WO2011/014503
PCT Pub. Date: Feb. 3, 2011

(65) Prior Publication Data
US 2012/0130113 A1     May 24, 2012

Related U.S. Application Data

(60) Provisional application No. 61/228,951, filed on Jul. 27, 2009.

(51) Int. Cl.
| C07C 253/30 | (2006.01) |
| C07C 201/12 | (2006.01) |
| C07C 1/32 | (2006.01) |
| C07C 17/263 | (2006.01) |
| C07C 209/68 | (2006.01) |

(52) U.S. Cl.
CPC .............. *C07C 201/12* (2013.01); *C07C 1/321* (2013.01); *C07C 17/263* (2013.01); *C07C 209/68* (2013.01); *C07C 253/30* (2013.01); *C07C 2523/72* (2013.01); *C07C 2531/28* (2013.01)

(58) Field of Classification Search
None
See application file for complete search history.

(56) References Cited

U.S. PATENT DOCUMENTS

| 2,684,967 | A | 7/1954 | Berg |
| 4,532,225 | A | 7/1985 | Tsao et al. |
| 5,160,500 | A | 11/1992 | Chu et al. |
| 5,208,335 | A | 5/1993 | Ramprasad et al. |
| 5,648,508 | A | 7/1997 | Yaghi et al. |
| 5,733,505 | A | 3/1998 | Goldstein et al. |
| 6,479,447 | B2 | 11/2002 | Bijl et al. |
| 6,501,000 | B1 | 12/2002 | Stibrany et al. |
| 6,617,467 | B1 | 9/2003 | Muller et al. |
| 6,624,318 | B1 | 9/2003 | Mueller et al. |
| 6,686,428 | B2 * | 2/2004 | Zhang et al. ................... 526/285 |
| 6,893,564 | B2 | 5/2005 | Mueller et al. |
| 6,929,679 | B2 | 8/2005 | Mueller et al. |
| 6,930,193 | B2 | 8/2005 | Yaghi et al. |
| 7,196,210 | B2 | 3/2007 | Yaghi et al. |
| 7,202,385 | B2 | 4/2007 | Mueller et al. |
| 7,279,517 | B2 | 10/2007 | Mueller et al. |
| 7,309,380 | B2 | 12/2007 | Mueller et al. |
| 7,343,747 | B2 | 3/2008 | Mueller et al. |
| 7,411,081 | B2 | 8/2008 | Mueller et al. |
| 7,524,444 | B2 | 4/2009 | Hesse et al. |
| 7,582,798 | B2 | 9/2009 | Yaghi et al. |
| 7,652,132 | B2 | 1/2010 | Yaghi et al. |
| 7,662,746 | B2 | 2/2010 | Yaghi et al. |
| 7,799,120 | B2 | 9/2010 | Yaghi et al. |
| 7,815,716 | B2 | 10/2010 | Mueller et al. |
| 8,480,955 | B2 | 7/2013 | Yaghi et al. |
| 8,709,134 | B2 | 4/2014 | Yaghi et al. |
| 8,735,161 | B2 | 5/2014 | Yaghi et al. |
| 8,742,152 | B2 | 6/2014 | Yaghi et al. |
| 2003/0004364 | A1 | 1/2003 | Yaghi et al. |
| 2003/0078311 | A1 | 4/2003 | Muller et al. |
| 2003/0148165 | A1 | 8/2003 | Muller et al. |
| 2003/0222023 | A1 | 12/2003 | Mueller et al. |
| 2004/0081611 | A1 | 4/2004 | Muller et al. |
| 2004/0225134 | A1 | 11/2004 | Yaghi et al. |
| 2004/0249189 | A1 | 12/2004 | Mueller et al. |
| 2004/0265670 | A1 | 12/2004 | Muller et al. |
| 2005/0004404 | A1 | 1/2005 | Muller et al. |
| 2005/0014371 | A1 | 1/2005 | Tsapatsis |
| 2005/0124819 | A1 | 6/2005 | Yaghi et al. |
| 2005/0154222 | A1 | 7/2005 | Muller et al. |
| 2005/0192175 | A1 | 9/2005 | Yaghi et al. |
| 2006/0057057 | A1 | 3/2006 | Muller et al. |

(Continued)

FOREIGN PATENT DOCUMENTS

| DE | 102005023856 A1 | 11/2006 |
| DE | 102005054523 A1 | 5/2007 |

(Continued)

OTHER PUBLICATIONS

Adamo et al., Journal of the American Chemical Society, 2006, vol. 28, pp. 6829.*
Moreno-Mañas et al., Journal of Organic Chemistry, 1996, vol. 16, pp. 2346-2351.*
Lakmini et al., Journal of Physical Chemistry, Jul. 2, 2008, vol. 112, pp. 12896-12903.*
Hassan et al., Chemical Reviews, 2002, vol. 102, pp. 1359-1469.*
Smith et al., Synlett, Jan. 2007, Issue 1, pp. 131-132.*

(Continued)

*Primary Examiner* — Laura L. Stockton
(74) *Attorney, Agent, or Firm* — Joseph R. Baker, Jr.; Gavrilovich, Dodd & Lindsey LLP

(57) ABSTRACT

The disclosure provides methods for the use of open metal frameworks to catalyze coupling reactions.

19 Claims, 8 Drawing Sheets

(56) References Cited

U.S. PATENT DOCUMENTS

| | | |
|---|---|---|
| 2006/0135824 A1 | 6/2006 | Mueller et al. |
| 2006/0154807 A1 | 7/2006 | Yaghi et al. |
| 2006/0185388 A1 | 8/2006 | Muller et al. |
| 2006/0252641 A1 | 11/2006 | Yaghi et al. |
| 2006/0252972 A1 | 11/2006 | Pilliod et al. |
| 2006/0287190 A1 | 12/2006 | Eddaoudi et al. |
| 2007/0068389 A1 | 3/2007 | Yaghi et al. |
| 2007/0202038 A1 | 8/2007 | Yaghi et al. |
| 2008/0017036 A1 | 1/2008 | Schultink et al. |
| 2008/0184883 A1 | 8/2008 | Zhou et al. |
| 2009/0155588 A1 | 6/2009 | Hesse et al. |
| 2010/0132549 A1 | 6/2010 | Yaghi et al. |
| 2010/0143693 A1 | 6/2010 | Yaghi et al. |
| 2010/0186588 A1 | 7/2010 | Yaghi et al. |
| 2010/0286022 A1 | 11/2010 | Yaghi et al. |
| 2011/0137025 A1 | 6/2011 | Yaghi et al. |

FOREIGN PATENT DOCUMENTS

| | | |
|---|---|---|
| EP | 1674555 A1 | 6/2006 |
| JP | 2007534658 A | 11/2007 |
| WO | 2004101575 A2 | 11/2004 |
| WO | 2006072573 A2 | 7/2006 |
| WO | 2006116340 A1 | 11/2006 |
| WO | 2007101241 A2 | 9/2007 |
| WO | 2008091976 A1 | 7/2008 |
| WO | 2008138989 A1 | 11/2008 |
| WO | 2008140788 A1 | 11/2008 |
| WO | 2009020745 A9 | 2/2009 |
| WO | 2009042802 A1 | 4/2009 |
| WO | 2009056184 A1 | 5/2009 |
| WO | 2009149381 A3 | 12/2009 |
| WO | 2010078337 A1 | 7/2010 |
| WO | 2010083418 A1 | 7/2010 |
| WO | 2010088629 A1 | 8/2010 |
| WO | 2010090683 A1 | 8/2010 |
| WO | 2010148276 A3 | 12/2010 |
| WO | 2010148296 A3 | 12/2010 |
| WO | 2010148374 A3 | 12/2010 |
| WO | 2011038208 A2 | 3/2011 |

OTHER PUBLICATIONS

Kim et al., CrystEngComm, 2014, Paper, "Isoreticular MOFs based on rhombic dodecahedral MOP as a tertiary building unit.", DOI:10.1039/c4ce00017j.*

Czaja, Alexander U. et al., "Inustrial applications of metal-organic frameworks," Chemical Society Reviews, Mar. 16, 2009, pp. 1284-1293, vol. 38, No. 5.

Demir A.S. et al., "Role of Copper Species in the Oxidation Dimerization of Arylborronic Acids: Synthesis of Symmetrical Biaryls," J. of Organic Chemistry, Dec. 26, 2003, pp. 10130-10134, vol. 68, No. 26.

Gonzales-Arellano C. et al., "Homogeneous and heterogenized Au(III) Schiff base-complexes as selective and general catalysts for self-coupling of aryl boronic acids," Chemical Communications, Apr. 21, 2005, pp. 1990-1992, No. 15.

Kirai, N., et al., "Homocoupling of arylboronic acids catalysed by 1,10-phenanthroline-ligated copper complexes in air," European J. of Organic Chemistry, Mar. 16, 2009, pp. 1864-1867.

Koza, D.J. et al., "An Efficient High Yielding Approach for the Homocoupling of Aryl Boronic Acids," Synthesis, Nov. 1, 2002, pp. 2183-2186, No. 15.

Llabres I. Xamena et al., "MOFs as catalysts: Activity, reusability and shape-selectivity of a Pd-containing MOF," J. of Catalysis, pp. 294-298, vol. 250, No. 2, 2007.

Patteux, Claudine, International Search Report and Written Opinion, PCT/US2010/043373, European Patent Office, Jun. 10, 2010.

Xiao Jia, Chinese Patent Application No. 201080021284.2; The State Intellectual Property Office of the People's Republic of China, Issue Date: Aug. 19, 2014.

Andrew et al., "Post-Synthetic Modification of Tagged MOFs," Angew. Chem. Int. Ed. 47:8482-8486 (2008).

Baharlou, Simin. International Preliminary Report on Patentability for PCT/US2009/046463. Date of Mailing: Dec. 16, 2010.

Banerjee et al., "High-Throughput Synthesis of Zeolitic Imidazolate Frameworks and Application to CO2 Capture," Science 319:939-943 (2008).

Banerjee et al., "Control of Pore Size and Functionality in Isoreticular Zeolitic Imidazolate Frameworks and their Carbon Dioxide Selective Capture Properties," J. Am. Chem. Soc. 131:3875-3877 (2009).

Barman et al., "Azulene Based Metal-Organic Frameworks for Strong Adsorption of H2," Chem. Commun. 46: 7981-7983 (2010).

Barton et al., "Tailored Porous Materials," Chem. Mater. 11:2633-2656 (1999).

Bloch et al., "Metal Insertion in a Microporous Metal-Organic Framework Lined with 2,2'-Bipyridine" J. Am. Chem. Soc. 132:14382-14384 (2010).

Braun et al., "1,4-Benzenedicarboxylate Derivatives as Links in the Design of Paddle-Wheel Units and Metal-Organic Frameworks," Chem. Commun. 24:2532-2533 (2001).

Britt et al., "Highly efficient separation of carbon dioxide by a metal-organic framework replete with open metal sites," Proc. Natl. Acad. Sci. USA 106:20637-20640 (2009).

Britt et al., "Ring-Opening Reactions Within Metal-Organic Frameworks," Inorg. Chem. 49:6387-6389 (2010).

Carlucci et al., "Nanoporous three-dimensional networks topologically related to cooperite from the self-assembly of copper(I)centres and teh 1,2,4,5-tetracyanobenzene," New J. Chem. 23(23):397-401 (1999).

Carlucci, Lucia et al., "Polycatenation, polythreading and polyknotting in coordination network chemistry" Coordination Chemistry Reviews 246, 2003, pp. 247-289.

Caskey et al., "Dramatic Tuning of CO2 Uptake via Metal Substitution in a Coordination Polymer with Cylindrical Pores," JACS 130(33):10870-10871 (2008).

Centrone et al., "Raman Spectra of Hydrogen and Deuterium Adsorbed on a Metal-Organic Framework," Chem. Phys. Lett. 411:516-519 (2005).

Chae et al., "Tertiary Building Units: Synthesis, Structure, and Porosity of a Metal-Organic Dendrimer Framework (MOD-1)," J. Am. Chem. Soc. 123:11482-11483 (2001).

Chae et al., "A Route to High Surface Area, Porosity and Inclusion of Large Molecules in Crystals," Nature427, 523-527 (2004); Featured in (1) Chemical & Engineering News magazine, Feb. 9, 2004, (2) BBC World Service, Feb. 4, (3) New Scientist, Feb. 4.

Chen et al., "Cu2(ATC)6H2O: Design of Open Metal Sites in Porous Metal-Organic Crystals (ATC: 1,3,5,7-adamantane tetracarboxylate)," J. Am. Chem. Soc. 122:11559-11560 (2000).

Chen et al., "Interwoven Metal-Organic Framework on a Periodic Minimal Surface with Extra-Large Pores," Science 291:1021-1023 (2001); Featured in Chemical and Engineering News, Feb. 21, 2001.

Chen et al., "Transformation of a Metal-Organic Framework from the NbO to PtS Net," Inorg. Chem. 41:181-183 (2005).

Chen et al., "High H2 Adsorption in a Microporous Metal-Organic Framework with Open-Metal Sites," Angew. Chem. Int. Ed. 44:4745-4749 (2005).

Chen et al., "A Microporous Metal-Organic Framework for Gas-Chomatographic Separation of Alkanes," Angew. Chem. Int. Ed. 45:1390-1393 (2006).

Cho et al., "A metal-organic framework material that functions as an enantioselective catalyst for olefin epoxidation," Chem. Comm. 24:2563-2565 (2006).

Choi et al., "Heterogeneity within Order in Crystals of a Porous Metal Organic Framework," J. Am. Chem. Soc. 133:11920-11923 (2011).

Cui et al., "IIn Situ Hydrothermal Growth of Metal-Organic Framework 199 Films on Stainless Steel Fibers for Solid-Phase Microextraction of Gaseous Benzene Homologues," Anal. Chem. 81(23):9771-9777 (2009).

Delgado-Friedrichs et al., "Three-Periodic Nets and Tilings: Regular and Quasiregular Nets," Acta Cryst. A59:22-27 (2003).

Delgado-Friedrichs et al. "What Do We Know About Three-Periodic Nets?," J. Solid State Chem. 178:2533-2554 (2005).

Delgado-Friedrichs et al. "Three-Periodic Nets and Tilings: Edge-Transitive Binodal Structures," Acta Cryst. 62:350-355 (2006).

(56) References Cited

OTHER PUBLICATIONS

Delgado-Friedrichs et al., "Taxonomy of Periodic Nets and the Design of Materials," Phys. Chem. 9:1035-1043 (2007).
Deng et al., "Multiple Functional Groups of Varying Ratios in Metal-Organic Frameworks," Science 327:846-850 (2010).
Deng et al., "Robust dynamics" Nature Chem. 2:439-443 (2010).
Doonan et al., "Isoreticular Metalation of Metal-Organic Frameworks," J. Am. Chem. Soc. 131:9492-9493 (2009).
Doonan, C., "Hydrogen Storage in Metal-Organic Frameworks," Annual Merit Review Proceedings of DOE Hydrogen Program, May 22, 2009.
Duren et al., "Design of New Materials for Methane Storage," Langmuir 20:2683-2689 (2004).
Eddaoudi et al., "Design and Synthesis of Metal-Organic Frameworks with Permanent Porosity," in Topics in Catalysis, G. A. Somorjai and J. M. Thomas, Eds., 9:105 (1999).
Eddaoudi et al., "Highly Porous and Stable Metal-Organic Framework: Structure Design and Sorption Properties," J. Am. Chem. Soc. 121:1391-1397 (2000).
Eddaoudi et al., "Porous Metal-Organic Polyhedra: 25 Å Cuboctahedron Constructed from Twelve Cu2(CO2)4 Paddle-Wheel Building Blocks," J. Am. Chem. Soc. 123:4368-4369 (2001).
Eddaoudi et al., "Modular Chemistry: Secondary Building Units as a Basis for the Design of Highly Porous and Robust Metal-Organic Carboxylate Frameworks" Acc. Chem. Res. 34:319-330 (2001).
Eddaoudi et al., "Geometric Requirements and Examples of Important Structures in the Assembly of Square Building Blocks," Proc. Natl. Acad. Sci. 99:4900-4904 (2002).
Eddaoudi et al., "Systematic Design of Pore Size and Functionality in Isoreticular Metal-Organic Frameworks and Application in Methane Storage," Science 295:469-472 (2002): Featured in (1) Chemical and Engineering News, Jan. 21, 2002, and (2) Chemical Insight magazine, Nov. 15, 2002.
Eddaoudi et al., "Cu2[o-Br-C6H3(CO2)2]2(H2O)2•(DMF)8(H2O)2: A Framework Deliberately Designed to have the NbO Structure Type," J. Am. Chem. Soc. 124:376-377 (2002).
Ferragut et al., "Positronium Formation in Porous Materials for Antihydrogen Production,"J. Phys. Conf. Ser. 225:1-8 (2010).
Furkawa et al., "Independent verification of the saturation hydrogen uptake in MOF-177 and establishment of a benchmark for hydrogen adsorption in metal-organic frameworks," J. Mater. Chem. 17:3197-3204 (2007).
Furukawa et al., "Control of Vertex Geometry, Structure Dimensionality, Functionality, and Pore Metrics in the Reticular Synthesis of Crystalline Metal-Organic Frameworks and Polyhedra," J. Am. Chem. Soc. 130:11650-11661 (2008).
Furukawa et al., "Storage of Hydrogen, Methane, and Carbon Dioxide in Highly Porous Covalent Organic Frameworks for Clean Energy Applications," J. Am. Chem. Soc. 25:8876-8883 (2009).
Furukawa et al., "Ultra-High Porosity in Metal-Organic Frameworks," Science 239:424-428 (2010).
Galli et al., "Adsorption of Harmful Organic Vapors by Flexible Hydrophobic Bis-pyrazolate Based MOFs," Chem. Mater. 22(5):1664-1672 (2010).
Glover et al., "MOF-74 building unit has a direct impact on toxic gas adsorption," J. Chem. Eng. Sci. 66:163-170 (2011).
Yaghi et al., "Construction of Microporous Materials from Molecular Building Blocks," Fundamental Materials Research, T. J. Pinnavaia and M. F. Thorpe, eds., vol. II, Plenum: New York, p. 111 (1995).
Yaghi et al., "Construction of Porous Solids from Hydrogen-Bonded Metal Complexes of 1,3,5-Benzenetricarboxylic Acid," J. Am. Chem. Soc., 1996, 118, 9096-9101.
Yaghi et al., "Conversion of Molecules and Clusters to Extended 3-D Cage and Channel Networks," Metal Containing Polymeric Materials, C. U. Pittman, C. E. Carraher, B. M. Culbertson, M. Zeldin, J. E. Sheets, Eds., Plenum: New York, p. 219 (1996).
Yaghi et al., "Selective Guest Binding by Tailored Channels in a 3-D Porous Zinc(II)-1,3,5-Benzenetricarboxylate Network," J. Am. Chem. Soc., 1997, 119, 2861-2868.

Yaghi et al., "Crystal Growth of Extended Solids by Nonaqueous Gel Diffusion," Chem. Mater., 1997, 9, 1074-1076.
Yaghi et al., "A Molecular Railroad with Large Pores: Synthesis and Structure of Ni(4,4'-bpy)2.5(H2O)2(ClO4)2•1.5(4,4'-bpy)2(H2O)," Inorg. Chem., 1997, 36, 4292-4293.
Yaghi et al., "Construction of a New Open-Framework Solid form 1,3,5-Cyclohexanetricarboxylate and Zinc(II) Building Blocks," J. Chem. Soc. Dalton Trans. 2383-2384 (1997).
Yaghi et al., "Designing Microporosity in Coordination Solids," Modular Chemistry, J. Michl, Ed., Kluwer: Boston, p. 663 (1997).
Yaghi et al., "Synthetic Strategies, Structure Patterns, and Emerging Properties in the Chemistry of Modular Porous Solids," Acc. Chem. Res. 31:474-484 (1998).
Yaghi et al., "Design of Solids from Molecular Building Blocks: Golden Opportunities for Solid State Chemistry," J. Solid State Chem. 152, 1-2 (2000).
Yaghi et al., "A Molecular World Full of Holes," Chem. Innov. p. 3 (2000).
Yaghi et al., "Reticular Synthesis and the Design of New Materials," Nature 423:705-714 (2003).
Yaghi, Omar., "Porous Crystals for Carbon Dioxide Storage," slide presentation at the Fifth Annual Conference on Carbon Capture & Sequestration, US Department of Energy on May 10, 2006 http://www.netl.doe.gov/publications/proceedings/06/carbon-seq/Tech%20Session%20193.pdf.
Yaghi et al., "Metal-Organic Frameworks: A Tale of Two Entanglements," Nature materials 6:92-93 (2007).
Yaghi, Omar, "Hydrogen Storage in Metal-Organic Frameworks," slide presentation to DOE Hydrogen Program 2007 Annual Merit Review, US Department of Energy, on May 15, 2007 at http://www.hydrogen.energy.gov/pdfs/review07/st_10_yaghi.pdf.
Yaghi et al., "Reticular Chemistry and Metal-Organic Frameworks for Clean Energy," MRS Bulletin 34:682-690 (2009).
Young, Lee W., International Search Report and Written Opinion, Date of Mailing of Report: May 7, 2008, International Application No. PCT/US08/51859.
Young, Lee W., "International search Report and Written Opinion," PCT/US08/06008, United States Patent & Trademark Office, Aug. 20, 2008.
Young, Lee W., International Search Report and Written Opinion, Date of Mailing: Dec. 2, 2008, International Application No. PCT/US08/77741.
Young, Lee W., International Search Report and Written Opinion, Date of Mailing: Jan. 12, 2009, International Application No. PCT/US08/70149.
Young, Jung Doo. International Search Report for PCT/US2010/050170. Date of Mailing: Jun. 8, 2011.
Zhang et al., "Docking in Metal-Organic Frameworks," Science 325:855-859 (2009).
Zhao, Wei. The First Office Action for Chinese Application No. 200880003157.2. The State Intellectual Property Office of the People's Republic of China. Issue Date: Aug. 5, 2011.
Mashiyama, Shinya, Office Action issued in Japanese Patent Application No. 2012-522962, Japanese Patent Office, Date of Mailing: May 27, 2014.
Gould et al., "The Amphidynamic Character of Crystalline MOF-5: Rotational Dynamics in a Free-Volume Environment," J. Am. Chem. Soc. 130:3246-3247 (2008).
Goebel, Matthias, Supplemental European Search Report and Written Opinion for EP08826913. Date of Completion of Search and Written Opinion: Nov. 10, 2010.
Goebel, Matthias, Supplemental European Search Report and Written Opinion for EP08754337. Date of Completion of Search and Written Opinion: Dec. 3, 2010.
Han, SS et al., "Improved designs of metal-organic frameworks for hydrogen storage" Angew. Chem. Int. Ed. 2007, 46, pp. 6289-6292.
Hayashi et al., "Zeolite A Imidazolate Frameworks," Nature Materials 6:501-506 (2007).
Hexiang et al., "Multiple Functional Groups of Varying Rations in Metal-Organic Frameworks," Science 327 (5967):846-850 (2010).
Honda, Masashi, International Preliminary Report on Patentability for PCT/US2008/051859. Date of Issuance of the Report: Jul. 28, 2009.

(56) References Cited

OTHER PUBLICATIONS

Howe, Patrick. International Search Report and Written Opinion for PCT/US2009/068849. Date of Mailing of the Search Report: Apr. 6, 2010.
Howe, Patrick. International Search Report and Written Opinion for PCT/US2010/022777. Date of Mailing: Jun. 7, 2010.
Huang et al., "Thermal Conductivity of Metal-Organic Framework 5 (MOF-5): Part II. Measurement," Int. J. Heat Mass Transfer 50:405-411 (2007).
Isaeva et al., "Metal-organic frameworks—new materials for hydrogen storage," Russian Journal of General Chemistry 77(4):721-739 (2007).
Jeong et al., "Asymmetric Catalytic Reactions by NbO-Type Chiral Metal-Organic Frameworks," Chem. Sci. 2:877-882 (2011).
Kaye et al., "Impact of Preparation and Handling on the Hydrogen Storage Properties of Zn4O(1,4-benzenedicarboxylate)3 (MOF-5)," J. Am. Chem. Soc. 129:14176-14177 (2007).
Kim et al., "Assembly of Metal-Organic Frameworks From Large Organic and Inorganic Secondary Building Units: New Examples and Simplifying Principles for Complex Structures," J. Am. Chem. Soc. 123:8239-8247 (2001).
Kim, Su Mi, International Search Report and Written Opinion, Date of Mailing: Feb. 24, 2010, International Application No. PCT/US09/46463.
Kim, Su Mi, International Search Report and Written Opinion for PCT/US2009/068731. Date of Mailing: Aug. 19, 2010.
Kim, Su Mi. International Search Report for PCT/US2010/039154. Date of Mailing: Feb. 23, 2011.
Klaes, Daphne. International Search Report and Written Opinion for PCT/US2010/021201. Date of Mailing: Apr. 27, 2010.
Kyoungmoo et al., "A Crystalline Mesoporous Coordination Copolymer with High Microporosity," Angew. Chem. Int. Ed. 47(4):677-680 (2008).
Lee, Ji Min. International Search Report for PCT/US2010/039284. Date of Mailing: Feb. 22, 2011.
Li et al., "Coordinatively Unsaturated Metal Centers in the Extended Porous Framewokr of Zn3(BDC)3·6CH3OH (BDC=1,4-Benzenedicarboxylate)," J. Am. Chem. Soc. 2186-2187 (1998).
Li et al., "Establishing Microporosity in Open Metal-Organic Frameworks: Gas Sorption Isotherms for Zn(BDC) (BDC=1,4-Benzenedicaroxylate)," J. Am. Chem. Soc. 120:8571-8572 (1998).
Li et al., "Design and Synthesis of an Exceptionally Stable and Highly Porous Metal-Organic Framework," 402:276-279 (1999); Featured in (1) Chemical and Engineering News (Nov. 22, 19999) and (2) Science News (Nov. 20, 1999).
Li et al., "20 Å [Cd4In16S35]14-Supertetrahedral T4 Clusters as Building Units in Decorated Cristobalite Frameworks," J. Am. Chem Soc. 123:4867-4868 (2001).
Li et al., "[Cd16In64S134]44-: 31-Å Tetrahedron with a Large Cavity," Angew. Chem. Int. Ed., 42:1819-1821 (2003).
Li et al., "A metal-organic framework replete with ordered donor-acceptor catenanes," Chem. Commun. 46:380-382 (2010).
Li et al., "A Catenated Strut in a Catenated Metal-Organic Framework," Angew. Chem. Int. Ed. 49:6751-6755 (2010).
Linder, Nora. International Preliminary Report on Patentability for PCT/US2010/022777. Date of Mailing: Aug. 11, 2011.
Long et al., "The Pervasive Chemistry of Metal-Organic Frameworks," Chem. Soc. Rev. 38:1213-1214 (2009).
Lu et al., "Synthesis and Structure of Chemically Stable Metal-Organic Polyhedra," J. Am. Chem. Soc. 131:(35) 12532-12533 (2009).
Mendoza-Cortes et al., "Adsorption Mechanism and Uptake of Methane in Covalent Organic Frameworks: Theory and Experiment," J. Phys. Chem. 114:10824-10833 (2010).
Michalitsch, Richard. International Search Report and Written Opinion for PCT/US2009/069700. Date of Mailing: May 7, 2010.
Millward et al., "Metal-Organic Frameworks with Exceptionally High Capacity for Storage of Carbon Dioxide at Room Temperature," J. Am. Chem. Soc. 127:17998-17999 (2005).
Morris et al., "Crystals as Molecules: Postsynthesis Covalent Functionalization of Zeolitic Imidazolate Frameworks," J. Am. Chem. Soc. 130:12626-12627 (2008).
Morris et al., "A Combined Experimental—Computational Investigation of Carbon Dioxide Capture in a Series of Isoreticular Zeolitic Imidazolate Frameworks," J. Am. Chem. Soc. 132:11006-11008 (2010).
Morris et al., "Postsynthetic Modification of a Metal-Organic Framework for Stabilization of a Hemiaminal and Ammonia Uptake," Inorg. Chem. 50:6853-6855 (2011).
Moyse, Ellen, International Preliminary Report on Patentability and Written Opinion, Date of Issuance of Report: Nov. 17, 2009, International Application No. PCT/US08/006008.
Mulhausen, Dorothee. International Preliminary Report on Patentability for PCT/US2009/069700. Date of Mailing: Jul. 7, 2011.
Mulhausen, Dorothee. International Preliminary Report on Patentability for PCT/US2010/021201. Date of Mailing Jul. 28, 2011.
Natarajan et al., "Non-carboxylate based metal-organic frameworks (MOFs) and related aspects," Current Opinion in Solid State and Materials Science 13(3-4):46-53 (2009).
Ni et al,. "Porous Metal-Organic Truncated Octahedron Constructed from Paddle-Wheel Squares and Terthiophene Links," J. Am. Chem. Soc. 127:12752-12753 (2005).
Nickitas-Etienne, Athina, International Preliminary Report on Patentability and Written Opinion, Date of Issuance of Report: Jan. 19, 2010, International Application No. PCT/US08/70149.
Nickitas-Etienne, Athina. International Preliminary Report on Patentability for PCT/US2008/07741. Date of issuance of this report: Mar. 30, 2010.
Nickitas-Etienne, Athina. International Preliminary Report on Patentability for PCT/US2009/068731. Date of Issuance of the Report: Jun. 21, 2011.
Nickitas-Etienne, Athina. International Preliminary Report on Patentability for PCT/US2009/068849. Date of Mailing: Jun. 30, 2011.
Oisaki et al., "A Metal-Organic Framework with Covalently Bound Organometallic Complexes," J. Am. Chem. Soc. 132:9262-9264 (2010).

\* cited by examiner

2θ (degree)

2θ (degree)

2θ (degree)

2θ (degree)

2θ (degree)

OXIDATIVE HOMO-COUPLING REACTIONS OF ARYL BORONIC ACIDS USING A POROUS COPPER METAL-ORGANIC FRAMEWORK AS A HIGHLY EFFICIENT HETEROGENEOUS CATALYST

CROSS REFERENCE TO RELATED APPLICATIONS

This application is a U.S. National Stage Application filed under 35 U.S.C. §371 and claims priority to International Application No. PCT/US10/43373, filed Jul. 27, 2010, which claims priority under 35 U.S.C. §119 from Provisional Application Ser. No. 61/228,951, filed Jul. 27, 2009, the disclosure of which is incorporated herein by reference.

STATEMENT AS TO FEDERALLY SPONSORED RESEARCH

This invention was made with Government support of Grant No. HDTRA1-08-1-0023 awarded by the Department of Defense—Defense Threat Reduction Agency and Grant No. DE-FG02-08ER15935 awarded by the Department of Energy. The U.S. government has certain rights in the invention.

TECHNICAL FIELD

The disclosure provides methods for the use of open metal frameworks to catalyze coupling reactions.

SUMMARY

The disclosure provides methods and composition comprising open frameworks with accessible metal sites (open-metal-sites) for catalyzing coupling reactions. The disclosure includes all open framework materials that are constructed from organic links bridged by multidentate organic or inorganic cores. Including all classes of open framework materials: covalent organic frameworks (COFs), zeolitic imidozolate frameworks (ZIFs), metal organic polyhedral (MOP) and metal organic frameworks (MOFs) and all possible resulting net topologies as described within the reticular chemistry structure resource.

The disclosure provides a method of using noble metal-based metal organic framework (MOP) or metal organic polyhedral (MOP) such as Cu-based and Pd-based frameworks as the catalyst for homo-coupling synthesis of biaryls. Under un-optimized conditions MOF and/or MOP framework reactions show up to 95% conversion and 90% selectivity. The MOF and/or MOP catalyst is proved to be chemically stable and has the long-sought-after heterogeneous catalytic characteristics.

In one embodiment, a noble metal-based homocoupling of arylboronic acids to synthesize substituted biaryls is provided. Such methods replace traditional methods such as dimerization of aryl-diazonium salts in Gomberg-Bachman reactions and homocoupling of aryl-halides in Ullmann reactions.

The methods and compositions of the disclosure can be used in catalysis and developing new approach for drug precursor synthesis.

The disclosure provides a method for synthesizing biaryls comprising contacting a metal organic framework (MOF) or metal organic polyhedral (MOP) with an aryl boronic acid compound under conditions wherein the MOF or MOP catalyze the synthesis of the biaryl through a homo-coupling reaction. In some embodiment, the method further comprises cupric acetate and the MOF or MOP comprises the metal copper. In yet another embodiment, the aryl bornic acid has the general structure:

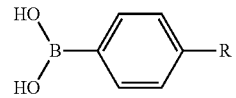

wherein R is selected from the group consisting of H, $NO_2$, CN, Cl, t-Bu, $N(CH_3)_2$ and substituted or unsubstituted napthyl. In one embodiment, the napthyl has the structure

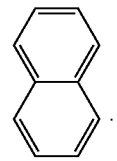

In yet another embodiment, the MOF or MOP comprises a linking ligands selected from the group consisting of:

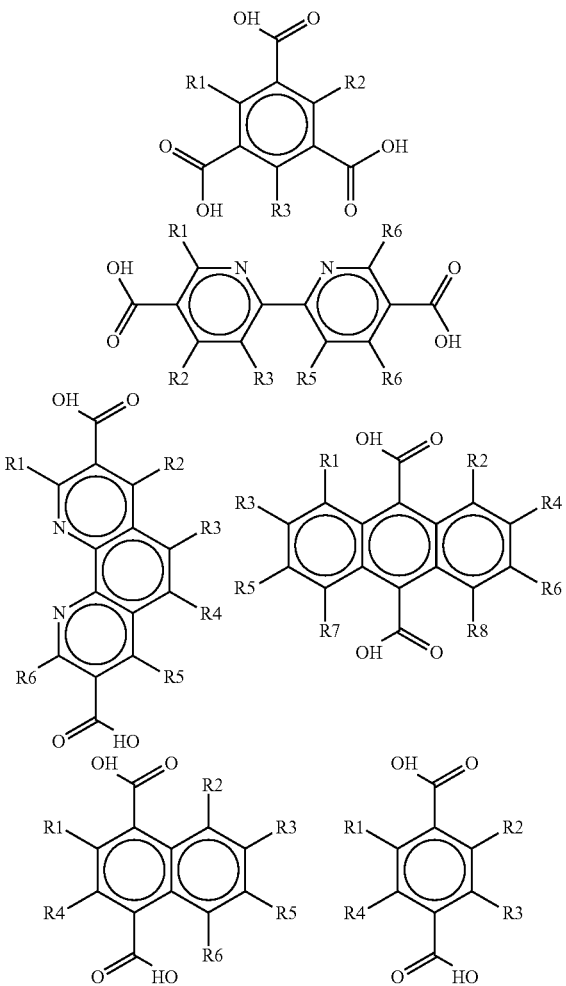

-continued

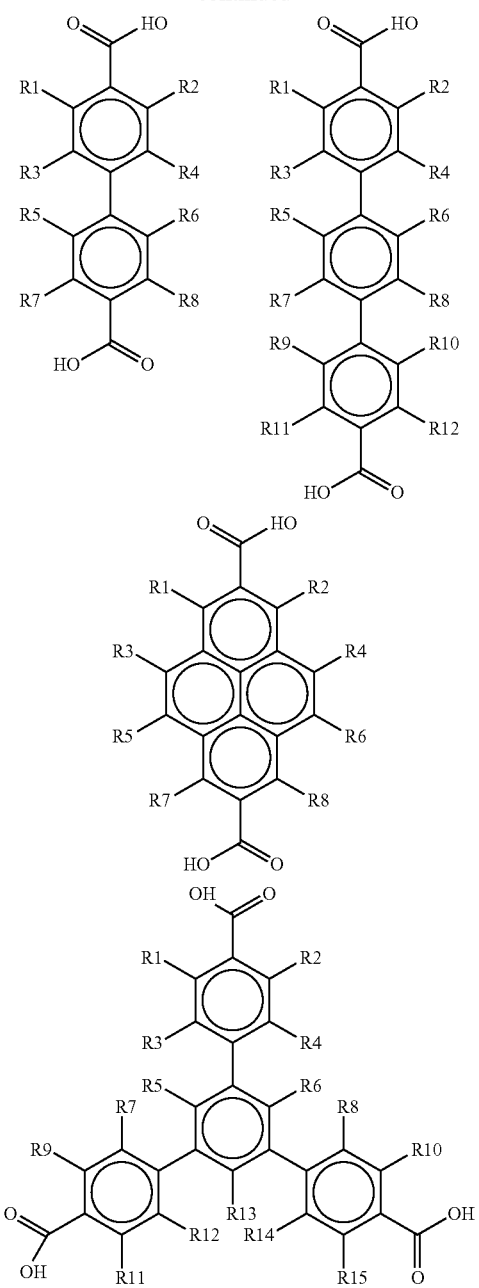

wherein R$_1$-R$_{15}$ may or may not be present and if present are independently selected from the group consisting of: —NH$_2$, —CN, —OH, =O, =S, —SH, —P, —Br, —Cl, —I, —F,

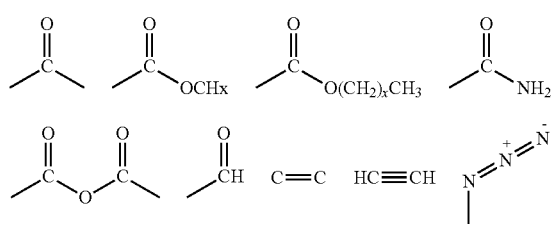

wherein X=1, 2, or 3. In yet another embodiment the linking moiety is

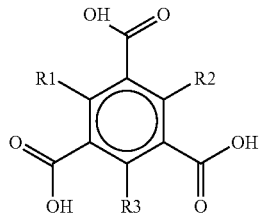

wherein R$_1$-R$_3$ may or may not be present and if present are independently selected from the group consisting of: —H, —NH$_2$, —CN, —OH, =O, =S, —SH, —P, —Br, —Cl, —I, —F,

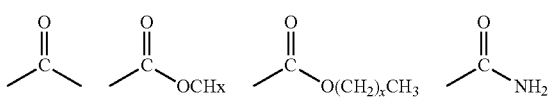

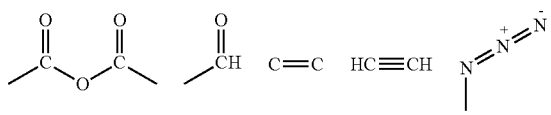

wherein X=1, 2, or 3. In yet another embodiment, the MOF comprises copper. In a specific embodiment, the MOF comprises a Cu$_3$(BTC)$_2$ (where BTC is benzene-1,3,5-tricarboxylate). In other embodiments, the MOF comprises a metal selected from the group consisting of Cr(II), Pb(II), Mn(IV), Ti(II) and Ni(II).

The disclosure also provide a reaction mixture comprising a metal organic framework (MOF) or metal organic polyhedral (MOP) and an aryl boronic acid. In some embodiments, the mixture further comprises cupric acetate. In some embodiments, the aryl bornic acid has the general structure:

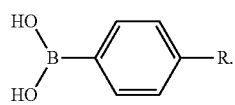

wherein R is selected from the group consisting of H, NO$_2$, CN, Cl, t-Bu, N(CH$_3$)$_2$ and substituted or unsubstituted napthyl. In one embodiment, the napthyl has the structure

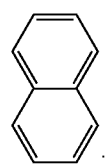

In yet other embodiment, the MOF or MOP comprises a linking ligands selected from the group consisting of:
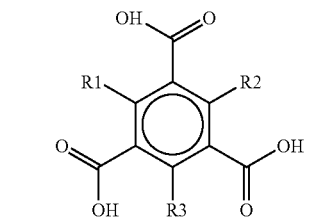
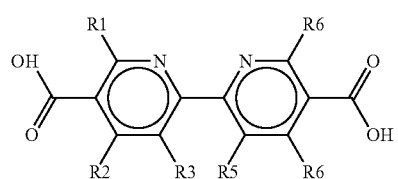
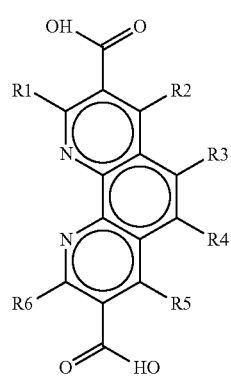
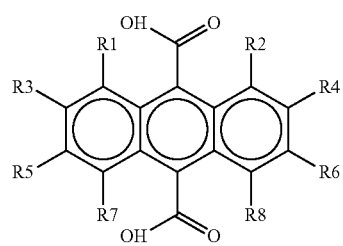
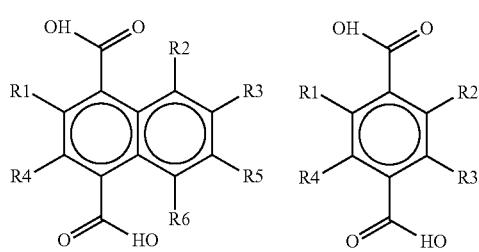
-continued
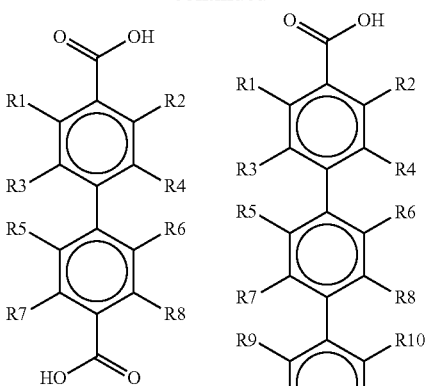
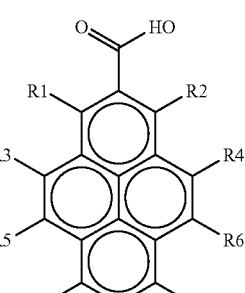
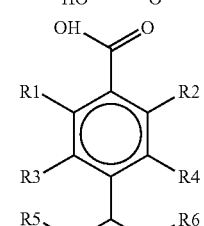
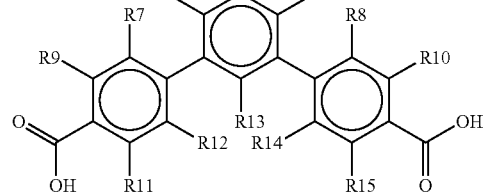
wherein $R_1$-$R_{15}$ may or may not be present and if present are independently selected from the group consisting of: —$NH_2$, —CN, —OH, =O, =S, —SH, —P, —Br, —Cl, —I, —F,
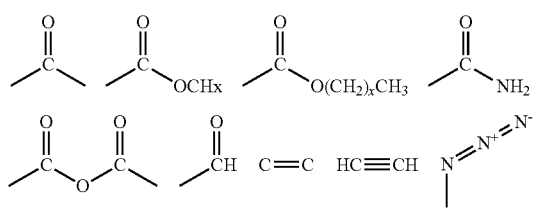

wherein X=1, 2, or 3. In one embodiment, the linking moiety is

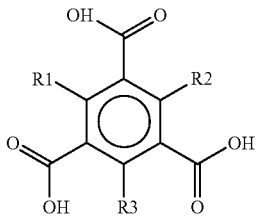

wherein $R_1$-$R_3$ may or may not be present and if present are independently selected from the group consisting of: —H, —NH$_2$, —CN, —OH, =O, =S, —SH, —P, —Br, —Cl, —I, —F,

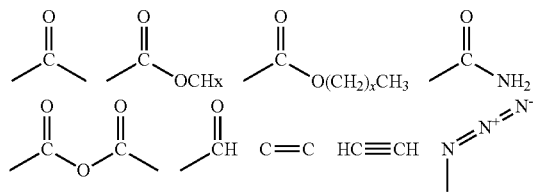

wherein X=1, 2, or 3. In one embodiment, the MOF comprises copper. In a specific embodiment, the MOF comprises a Cu$_3$(BTC)$_2$ (where BTC is benzene-1,3,5-tricarboxylate). In yet other embodiments, the MOF comprises a metal selected from the group consisting of Cr(II), Pb(II), Mn(IV), Ti(II) and Ni(II).

The details of one or more embodiments of the invention are set forth in the accompanying drawings and the description below. Other features, objects, and advantages of the invention will be apparent from the description and drawings, and from the claims.

DETAILED DESCRIPTION

Figure 1:
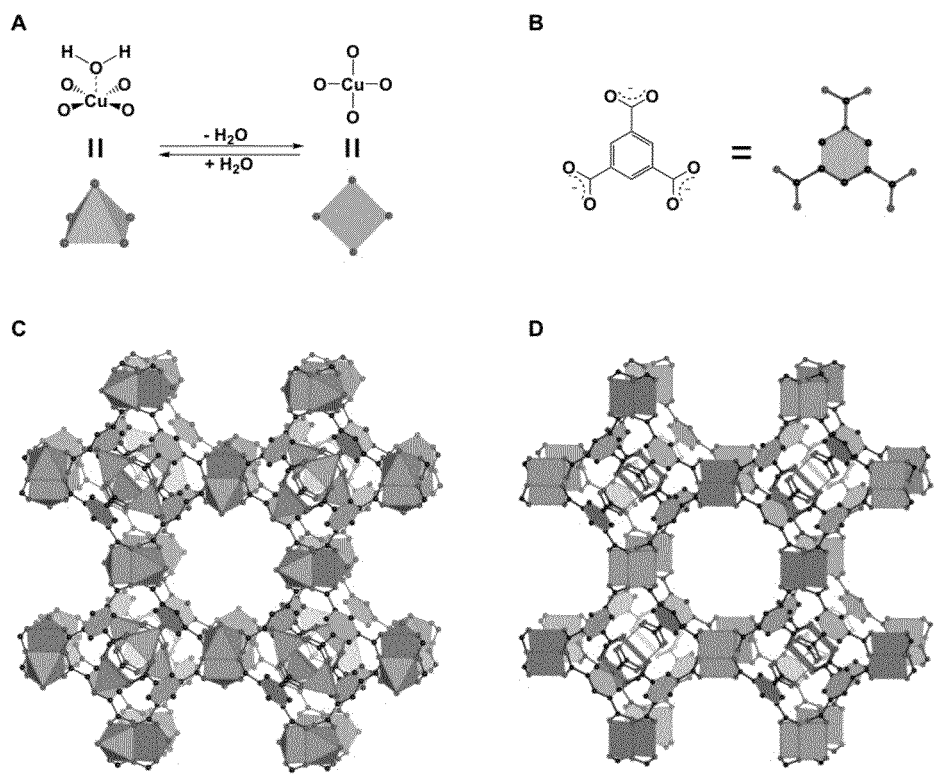
FIG. 1A-D shows atomic connectivity and structure of crystalline Cu$_3$(BTC)$_2$. (A) Cu sites in as-synthesized (left) and activated Cu$_3$(BTC)$_2$ frameworks; (B) BTC link; (C) structure of as-synthesized Cu$_3$(BTC)$_2$; and (D) structure of activated Cu$_3$(BTC)$_2$. Cu, O and C are shown. All H atoms are omitted for clarity.

As used herein and in the appended claims, the singular forms "a," "and," and "the" include plural referents unless the context clearly dictates otherwise. Thus, for example, reference to "a framework" includes a plurality of such frameworks and reference to "the metal" includes reference to one or more metals and equivalents thereof known to those skilled in the art, and so forth.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Unless defined otherwise, all technical and scientific terms used herein have the same meaning as commonly understood to one of ordinary skill in the art to which this disclosure belongs. Although any methods and reagents similar or equivalent to those described herein can be used in the practice of the disclosed methods and compositions, the exemplary methods and materials are now described.

All publications mentioned herein are incorporated herein by reference in full for the purpose of describing and disclosing the methodologies, which are described in the publications, which might be used in connection with the description herein. The publications discussed above and throughout the text are provided solely for their disclosure prior to the filing date of the present application. Nothing herein is to be construed as an admission that the inventors are not entitled to antedate such disclosure by virtue of prior disclosure.

The synthesis of functionalized biaryls is currently an area of great interest and importance, as these compounds account for some of the most critical structural units in natural products, drugs and functional materials. Homo-coupling of arylboronic acids using noble metal catalysts has proved to be a useful method for the synthesis of symmetrical biaryls. Although efficient, their cost and stability dramatically limit the viability of Pd-based catalysts in many applications. Another method employs Gomberg-Bachmann and Ullmann reactions which require high temperatures (ca. 200° C.) and thus severely limit their compatibility with many functional groups (—NO$_2$ and —CN).

The disclosure demonstrates that MOF and MOP structures serve as an outstanding alternative to precious metal dominated Suzuki homo-coupling reactions with comparable yield and selectivity. The methods and compositions of the disclosure also show great potential of MOF chemistry as it introduces desired complexity and functionality along with exceptional porosity. Specifically, such complexity offered by uniquely connected active centers behave in a favored pattern, which is unprecedented comparing to its molecular counter parts. The catalyst may also be modified in a way to allow the Chan-Lam Coupling, which is a side product of the desired homocoupling reaction and is equally valuable for synthesis.

The disclosure demonstrates the methods and compositions of the disclosure on a group of selected MOFs/MOPs—MOF-5, MOF-177, MIL-53, MOF-199 and MOP-OH (Cu-based). However, it will be apparent from the disclosure other MOF and MOP frameworks that can be utilized in methods of the disclosure.

The disclosure provides a method for homo-coupling synthesis of biaryls using a metal-containing metal-organic frameworks (MOFs), e.g., $Cu_3(BTC)_2$ (where BTC is benzene-1,3,5-tricarboxylate), as the catalyst. Under un-optimized conditions, use of this MOF catalyst in the homo-couplings of arylboronic acids functionalized with, e.g., —H, —$NO_2$, —CN, —Cl, -t-Bu- and -$Me_2$N, and 1-naphthylboronic acid result in up to 92% yield. The MOF catalyst offers remarkably superior attributes as a heterogeneous catalyst that are endowed by its highly ordered and open structure; aspects that put its performance on par with the homogeneous catalysts. In addition the MOF catalyst has all the advantages associated with the variations that can be made on the MOF constituents. A description of some of these advantages and attributes are shown in Table 1.

Other transition metals, such as Cr(II), Pb(II), Mn(IV), Ti(II) and Ni(II) have been used to accelerate this homo-coupling reaction, however other co-catalysts and environmentally harmful additives need to be added to facilitate efficient turnover. Cu-based compounds are known to catalyze some coupling reactions (e.g., Glaser Coupling and Chan-Lam Coupling) under homogeneous conditions and consequently high yields can be achieved. In order to maintain such performance in heterogeneous catalytic systems, materials with well-defined porous structures with mono-dispersed and fully accessible metal centers are needed. MOFs are a new class of porous crystals with exceptional porosity and record-breaking surface areas (up to 5,900 $m^2$ $g^{-1}$).

To illustrate embodiments of the disclosure, $Cu_3(BTC)_2$, a copper-based MOF, was used as the catalyst for various oxidative homo-coupling reactions. As shown in FIG. 1, the structure of this MOF is constructed from copper paddle-wheel secondary building units (SBUs). The 12 carboxylate oxygen atoms from the two benzenetricarboxylic acid (BTC) groups bind to four coordination sites for each of the three Cu ions of the formula unit. Each metal completes its pseudooctahedral coordination sphere with an axial $H_2O$ ligand along the Cu—Cu axis. Water molecules can be easily removed by heating under vacuum (FIG. 1A), which leads to open copper centers that are mono-dispersed throughout the pores (FIG. 1D). The copper centers have been shown to be Lewis acidic and they can be coordinated by various molecules. Such open metal centers in highly porous open framework may accelerate the initial coordination of amine and the following trans-metallation.

TABLE 1

Comparison of Pd-based catalyst and MOF catalyst $(HO)_2B$—⟨ ⟩—R $\xrightarrow{\text{Catalyst, Oxidant}}$ R—⟨ ⟩—⟨ ⟩—R

| | Pd-based Catalyst | MOF Catalyst |
| --- | --- | --- |
| Example | $(SiPr)Pd(OAc)_2(H_2O)^{(4)}$ | $Cu_3(BTC)_2$ |
| Metal | Pd(II) | Cu(II) |
| Ligand | [SiPr carbene ligand structure] | [BTC ligand structure] |
| Oxidant | [benzoquinone structure] | Air |
| Catalyst Type | Homogeneous | Heterogenous |
| Reusability | Low | High |
| Active Site Accessibility | High | High |
| Diffusion Rate | High | High |
| Structural Tunability | Medium | High |

Figure 3:
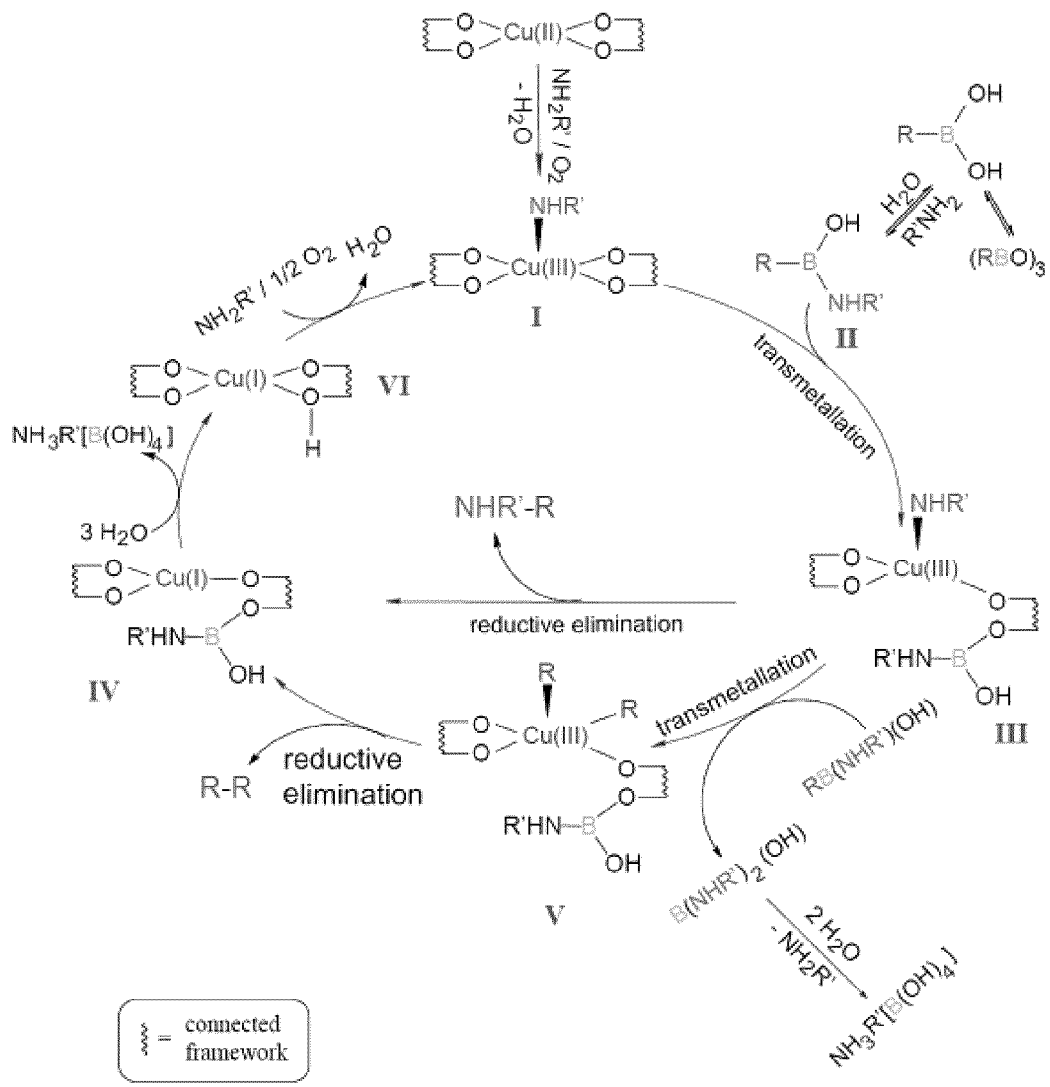
FIG. 3 shows the proposed mechanism for the Oxidative Homo-coupling catalyzed by Cu$_3$(BTC)$_2$.
Figure 4:
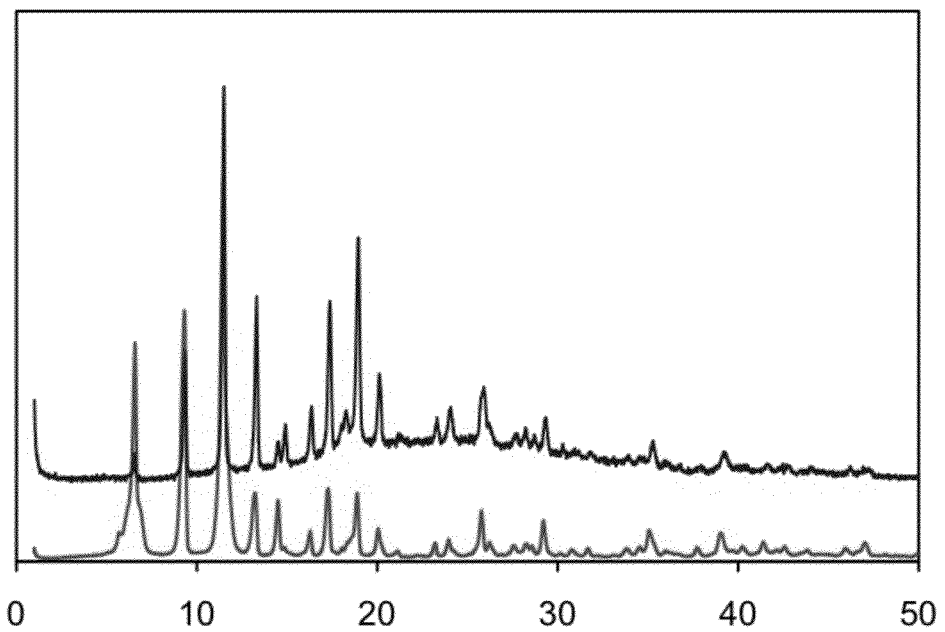
FIG. 4 shows a comparison of the experimental PXRD patterns of fresh Cu$_3$(BTC)$_2$ (bottom) and Cu$_3$(BTC)$_2$ after homo-coupling of phenylboronic acid (top).
Figure 5:
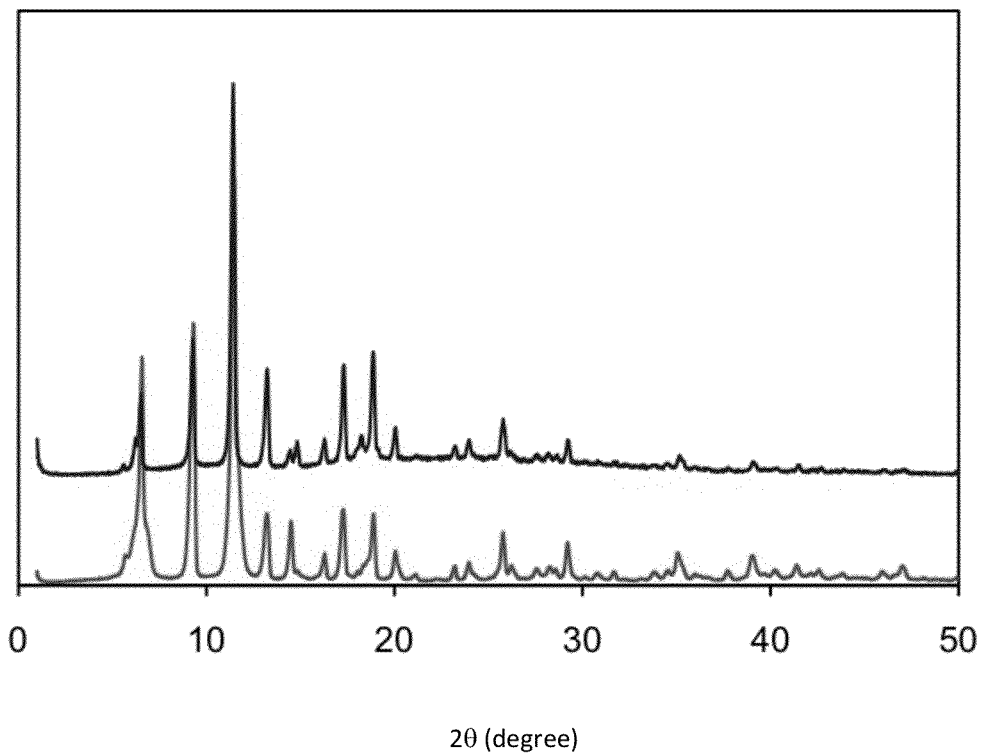
FIG. 5 shows a comparison of the experimental PXRD patterns of fresh Cu$_3$(BTC)$_2$ (bottom), and Cu$_3$(BTC)$_2$ after homo-coupling of 4-nitrophenylboronic acid (top).
Figure 6:
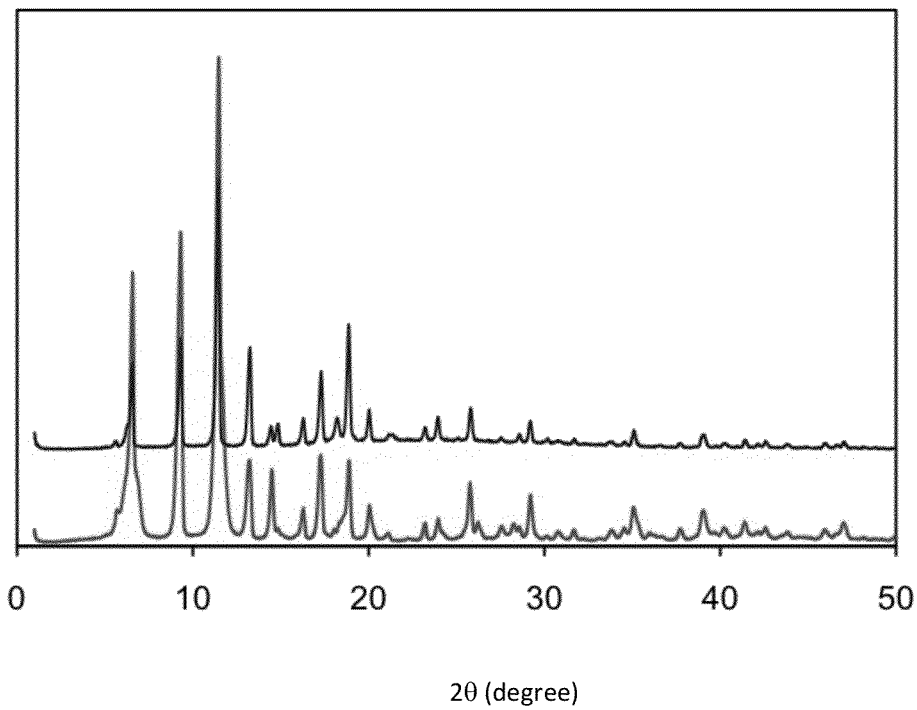
FIG. 6 shows a comparison of the experimental PXRD patterns of fresh Cu$_3$(BTC)$_2$ (bottom), and Cu$_3$(BTC)$_2$ after homo-coupling of 4-cyanophenylboronic acid (top).
Figure 7:
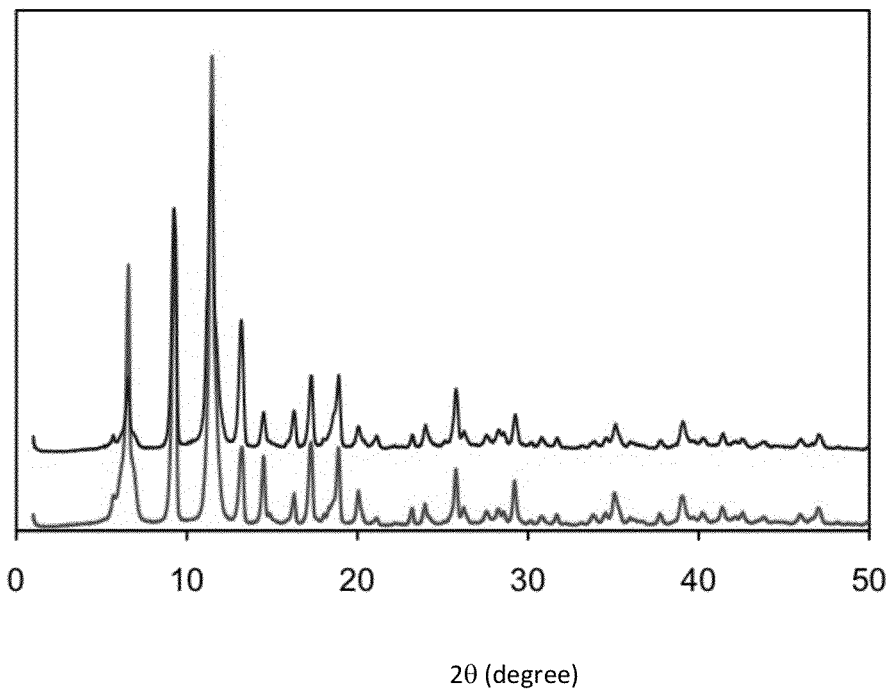
FIG. 7 shows a comparison of the experimental PXRD patterns of fresh Cu$_3$(BTC)$_2$ (bottom), and Cu$_3$(BTC)$_2$ after homo-coupling of 4-chlorophenylboronic acid (top).
Figure 8:
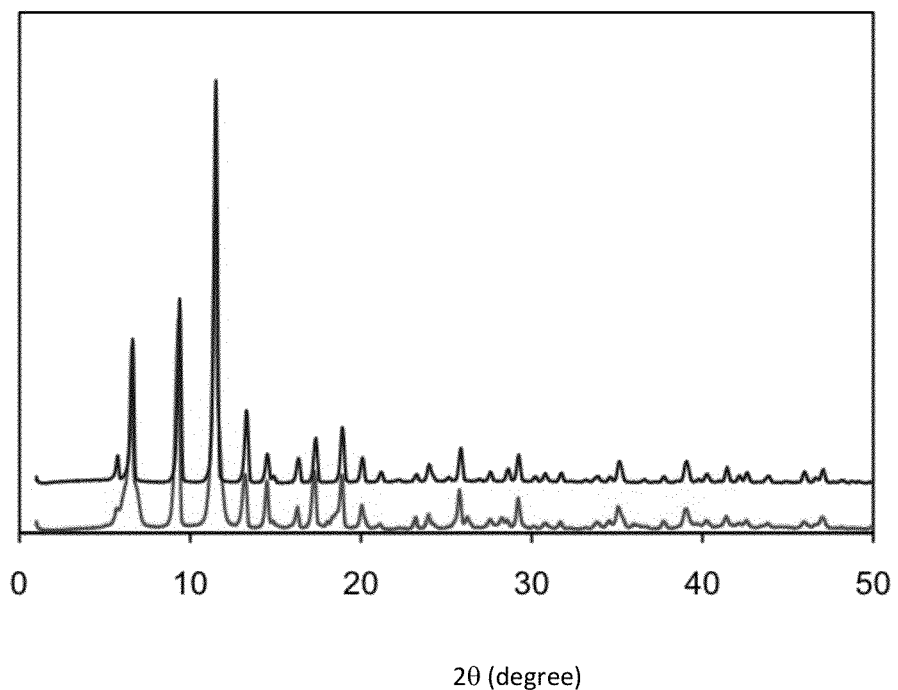
FIG. 8 shows a comparison of the experimental PXRD patterns of fresh Cu$_3$(BTC)2 (bottom), and Cu3(BTC)$_2$ after homo-coupling of 4-tert-butylphenylboronic acid (top).
Figure 9:
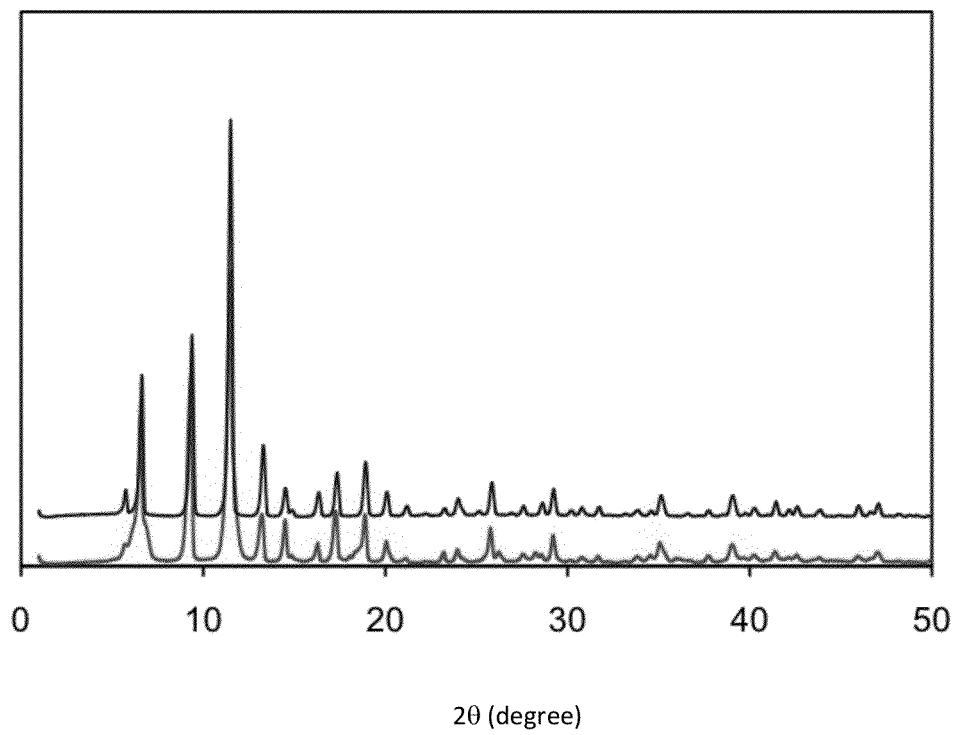
FIG. 9 shows a comparison of the experimental PXRD patterns of fresh Cu$_3$(BTC)$_2$ (bottom), and Cu$_3$(BTC)$_2$ after homo-coupling of 4-(dimethylamino)-phenylboronic acid (top).
Figure 10:
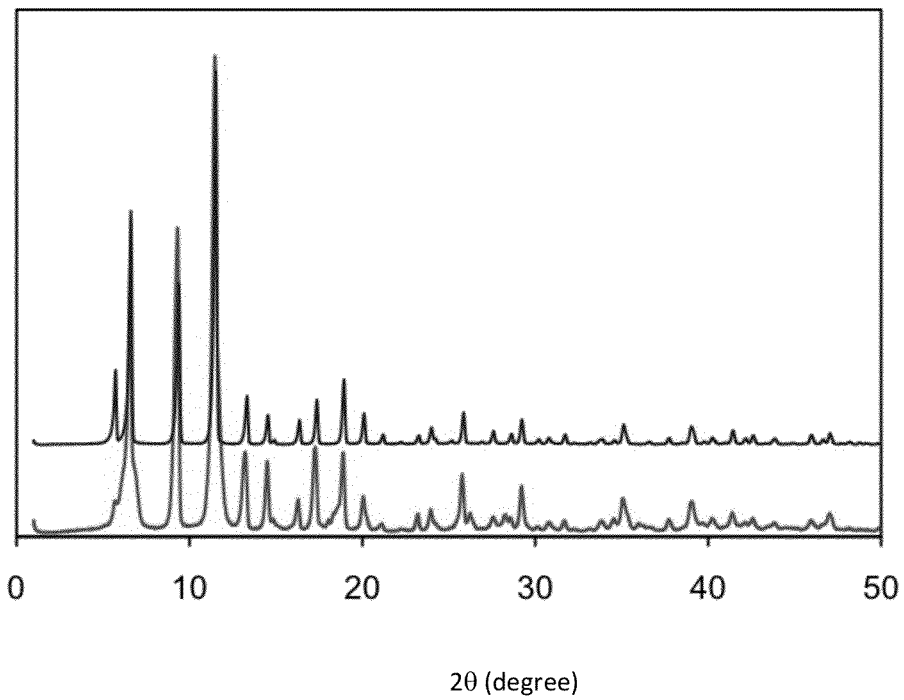
FIG. 10 shows a comparison of the experimental PXRD patterns of fresh Cu$_3$(BTC)$_2$ (bottom), and Cu3(BTC)$_2$ after homo-coupling of 1-naphthylboronic acid (top).

FIG. 3 depicts a proposed mechanism of action of the MOF in the synthesis of biaryls. The copper paddlewheel in the framework is coordinated by the base, followed by being oxidized by $O_2$ to form the catalytic copper (III) species I. Transmetallation of I with aryl boronic acid gives rise to complex II. The subsequent reductive elimination at the copper center leads to the Chan-Lam coupling product R—NHR' and the copper (I) species IV. On the other hand, a second transmetallation of complex II with aryl boronic acid produces III, which subsequently forms species IV and the homo-coupling product R—R by a reductive elimination reaction. Hydrolysis of species IV forms intermediate V and borate anion (evidenced by an $^{11}B$ NMR shift of 3.69 ppm).[13] The catalytic cycle was fulfilled by an oxidation reaction of V to regenerate the catalytic active species I.

As noted the Cu(II) core is linked using a linking ligand or moiety. The linking ligand or moiety can be any number of different compounds as described below. In the specific examples provided herein, the linking ligand/moiety is a BTC compound. Furthermore, it will be recognized that the linking ligand/moiety may be further functionalized as described below.

As used herein, a "core" refers to a repeating unit or units found in a framework. Such a framework can comprise a homogenous repeating core or a heterogeneous repeating core structure. A core comprises a metal or cluster of metals and a linking moiety. A plurality of cores linked together defines a framework.

The term "cluster" refers to identifiable associations of 2 or more atoms. Such associations are typically established by some type of bond—ionic, covalent, Van der Waal, and the like.

A "linking cluster" refers to a one or more reactive species capable of condensation comprising an atom capable of forming a bond between a linking moiety substructure and a metal group or between a linking moiety substructure and another linking moiety substructure. Examples of such species are selected from the group consisting of a boron, oxygen, carbon, nitrogen, and phosphorous atom. In some embodiments, the linking cluster may comprise one or more different reactive species capable of forming a link with a bridging oxygen atom. For example, a linking cluster can comprise $CO_2H$, $CS_2H$, $NO_2$, $SO_3H$, $Si(OH)_3$, $Ge(OH)_3$, $Sn(OH)_3$, $Si(SH)_4$, $Ge(SH)_4$, $Sn(SH)_4$, $PO_3H$, $AsO_3H$, $AsO_4H$, $P(SH)_3$, $As(SH)_3$, $CH(RSH)_2$, $C(RSH)_3$, $CH(RNH_2)_2$, $C(RNH_2)_3$, $CH(ROH)_2$, $C(ROH)_3$, $CH(RCN)_2$, $C(RCN)_3$, $CH(SH)_2$, $C(SH)_3$, $CH(NH_2)_2$, $C(NH_2)_3$, $CH(OH)_2$, $C(OH)_3$, $CH(CN)_2$, and $C(CN)_3$, wherein R is an alkyl group having from 1 to 5 carbon atoms, or an aryl group comprising 1 to 2 phenyl rings.

A "linking moiety" refers to a mono-dentate or polydentate compound that, through a linking cluster, bind a metal or a plurality of metals, respectively. Generally a linking moiety comprises a substructure having an alkyl or cycloalkyl group, comprising 1 to 20 carbon atoms, an aryl group comprising 1 to 5 phenyl rings, or an alkyl or aryl amine comprising alkyl or cycloalkyl groups having from 1 to 20 carbon atoms or aryl groups comprising 1 to 5 phenyl rings, and in which a linking cluster is covalently bound to the substructure. A cycloalkyl or aryl substructure may comprise 1 to 5 rings that comprise either of all carbon or a mixture of carbon with nitrogen, oxygen, sulfur, boron, phosphorus, silicon and/or aluminum atoms making up the ring. Typically the linking moiety will comprise a substructure having one or more carboxylic acid linking clusters covalently attached.

As used herein, a line in a chemical formula with an atom on one end and nothing on the other end means that the formula refers to a chemical fragment that is bonded to another entity on the end without an atom attached. Sometimes for emphasis, a wavy line will intersect the line.

In one embodiment, the linking moiety substructure is selected from any of the following:

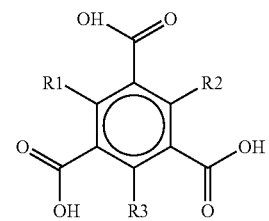

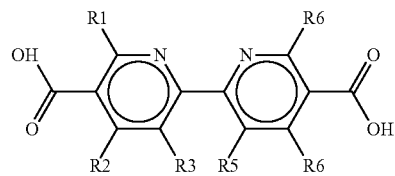

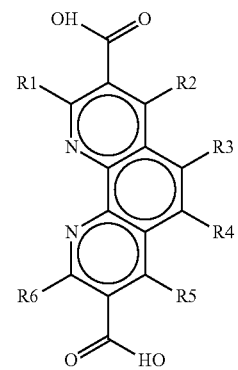

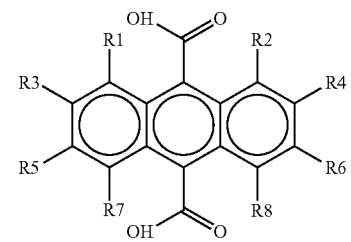

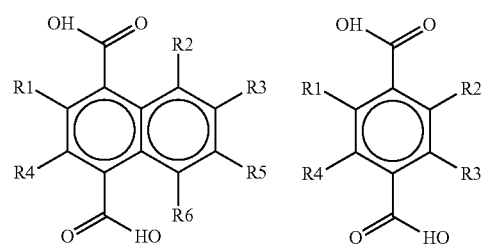

typically comprises at least one 5-membered ring with a nitrogen in the one position and three position of the 5-membered ring, which forms the linking moiety or bridge between two metal ions. The imidazole ring can be further functionalized to form benzimidazoles, triazole, bensotriazole, tetrazole, guanine, xanthine and hypoxanthine derivatives. For example, the following linking moieties can be used in the formation of catalytic frameworks of the disclosure:

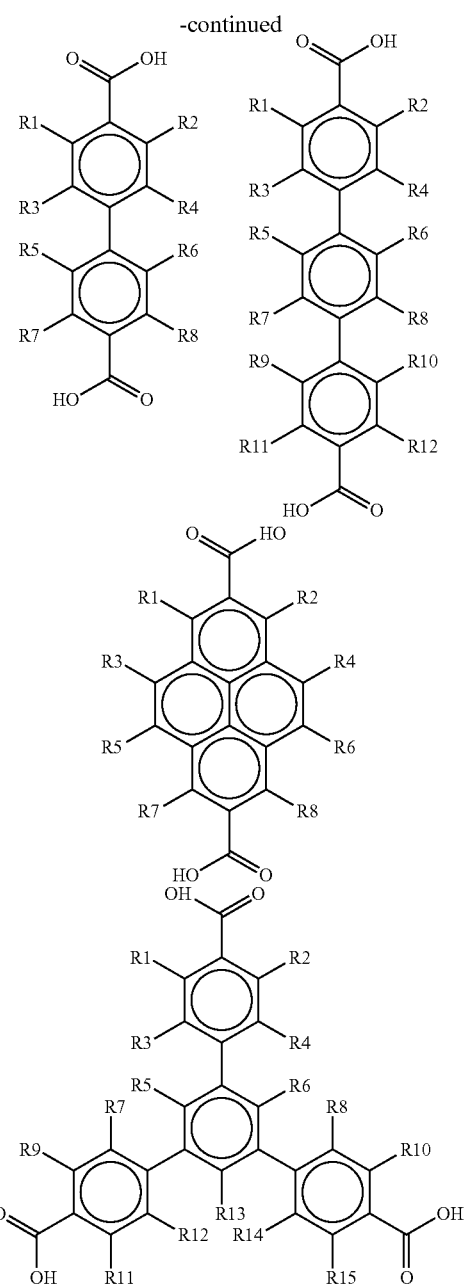

wherein $R_1$-$R_{15}$ may or may not be present and if present are independently selected from the group consisting of: —$NH_2$, —CN, —OH, =O, =S, —SH, —P, —Br, —Cl, —I, —F,

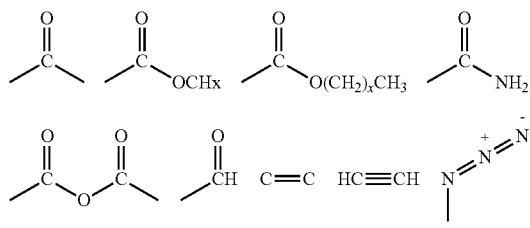

wherein X=1, 2, or 3.

In some embodiments, the framework used in the catalysis has a zeolitic structure. In such embodiments, the organic link

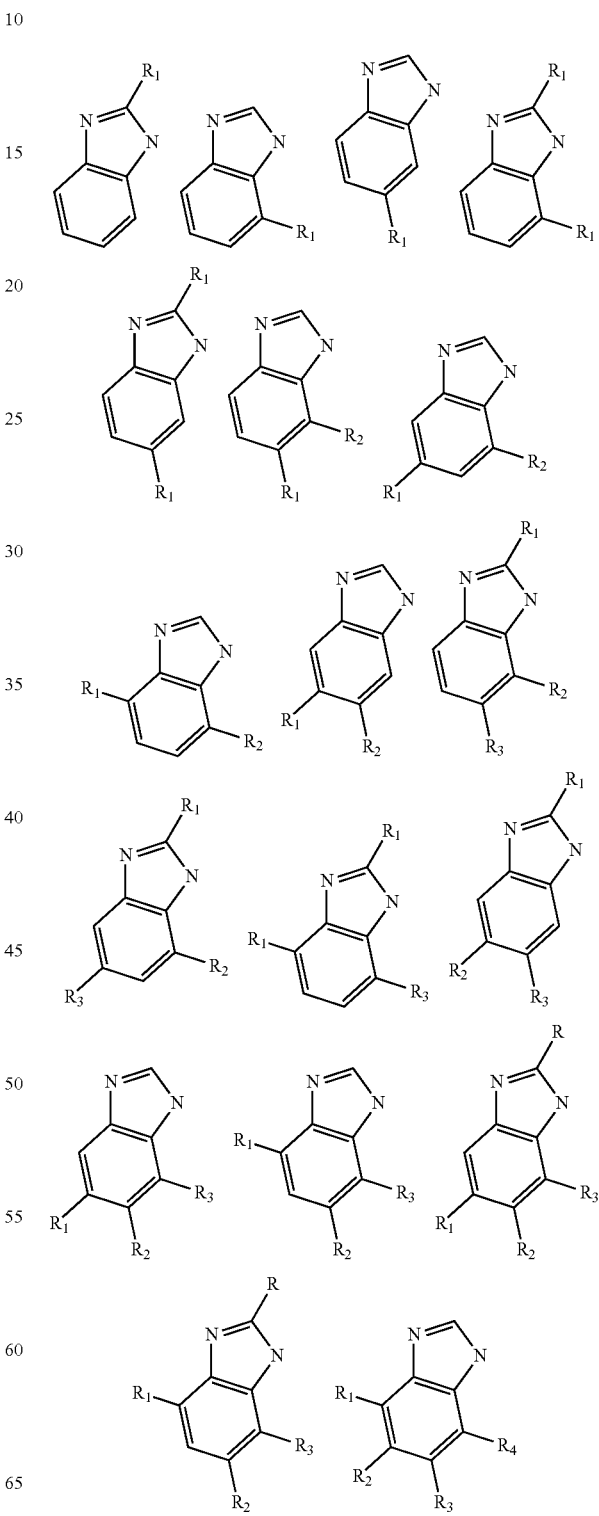

-continued

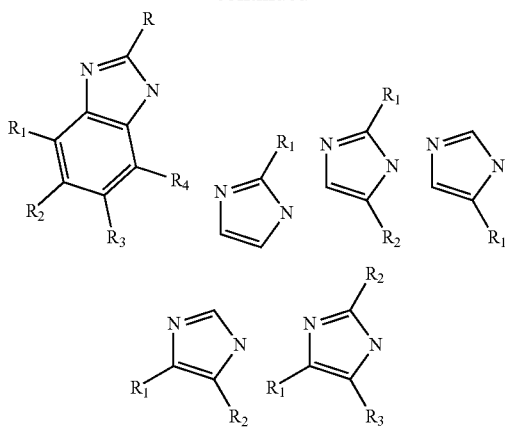

wherein R-R$_4$ is —H, —NH$_2$, —COOH, —CN, —NO$_2$, —F, —Cl, —Br, —S, —O, —SH, —SO$_3$H, —PO$_3$H$_2$, —OH, —CHO, —CS$_2$H, —SO$_3$H, —Si(OH)$_3$, —Ge(OH)$_3$, —Sn(OH)$_3$, —Si(SH)$_4$, —Ge(SH)$_4$, —Sn(SH)$_4$, —PO$_3$H, —AsO$_3$H, —AsO$_4$H, —P(SH)$_3$, —As(SH)$_3$, —CH(RSH)$_2$, C(RSH)$_3$, —CH(RNH$_2$)$_2$, —C(RNH$_2$)$_3$, —CH(ROH)$_2$, —C(ROH)$_3$, CH(RCN)$_2$, —C(RCN)$_3$

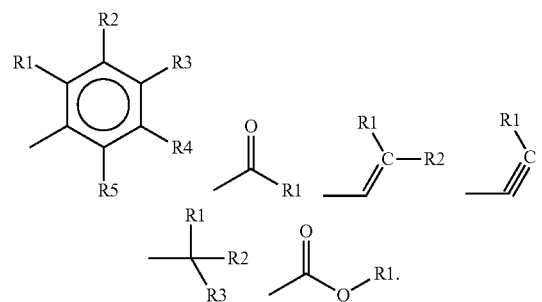

In yet another embodiment, the substructure can comprise substituted or unsubstituted aromatic rings, substituted of unsubstituted heteroacromatic rings, substituted or unsubstituted nonaromatic rings, substituted or unsubstituted nonaromatic heterocyclic rings, or saturated or unsaturated, substituted or unsubstituted, hydrocarbon groups. The saturated or unsaturated hydrocarbon groups may include one or more heteroatoms. For example a linking moiety can comprise the following structures:

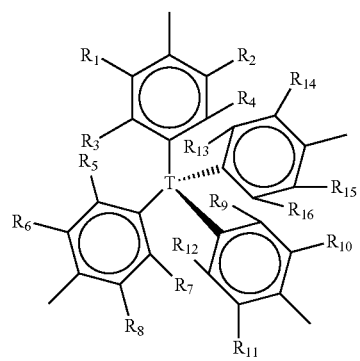

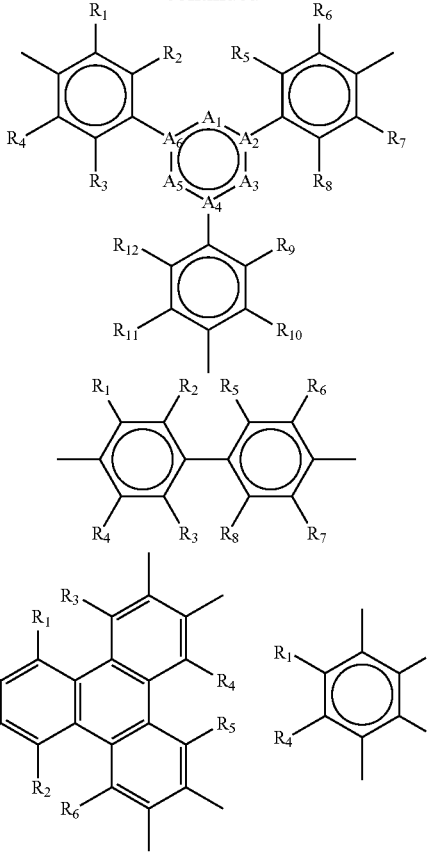

wherein A$_1$, A$_2$, A$_3$, A$_4$, A$_5$, and A$_6$ are each independently absent or any atom or group capable of forming a sable ring structure and R$_1$, R$_2$, R$_3$, R$_4$, R$_5$, R$_6$, R$_7$, R$_8$, R$_9$, R$_{10}$, R$_{11}$, R$_{12}$, R$_{13}$, R$_{14}$, R$_{15}$, and R$_{16}$ are each independently H, alkyl, aryl, OH, alkoxy, alkenes, alkynes, phenyl and substitutions of the foregoing, sulfur-containing groups (e.g., thioalkoxy), silicon-containing groups, nitrogen-containing groups (e.g., amides), oxygen-containing groups (e.g., ketones, and aldehydes), halogen, nitro, amino, cyano, boron-containing groups, phosphorus-containing groups, carboxylic acids, or esters. In one embodiment, R$_1$, R$_2$, R$_3$, R$_4$ are each independently selected from the group consisting of NH$_2$, CN, OH, =O, =S, SH, P, Br, CL, I, F,

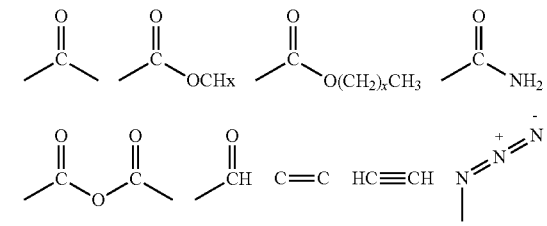

wherein X=1, 2, or 3.

All of the foregoing linking moieties that possess appropriate reactive groups can be chemically transformed by a suitable reactant post framework synthesis to further functionalize the framework. By modifying the organic links within the framework post-synthesis, access to function groups there were previously inaccessible or accessible only through great difficulty and/or cost is possible and facile. Post framework reactants include all known organic transformations and their respective reactants; rings of 1-20 carbons with functional groups including atoms such as N, S, O. All metals that may chelate to and add functional groups; or a combination of previously existing and newly added functional groups. All reactions that result in tethering an organometallic complex to the framework for use, for example, as a heterogenous catalyst.

A post framework reactant refers to any organic reactant. Rings of 1-20 carbons with functional groups comprising atoms such as N, S, O, and P are useful. In addition, metal and metal containing compounds that may chelate to and add functional groups or a combination of previously existing and newly added functional groups are also useful. Reactions that result in the tethering of organometallic complexes to the framework for use as, for example, a heterogeneous catalyst can be used. For example, converting a reactive side group in a linking agent to an alcohol followed by reacting the group with an alkali earth metal to generate a metal alkoxide is provided.

Examples of post framework reactants include, but are not limited to, heterocyclic compounds. In one embodiment, the post framework reactant can be a saturated or unsaturated heterocycle. The term "heterocycle" used alone or as a suffix or prefix, refers to a ring-containing structure or molecule having one or more multivalent heteroatoms, independently selected from N, O and S, as a part of the ring structure and including at least 3 and up to about 20 atoms in the ring(s). Heterocycle may be saturated or unsaturated, containing one or more double bonds, and heterocycle may contain more than one ring. When a heterocycle contains more than one ring, the rings may be fused or unfused. Fused rings generally refer to at least two rings share two atoms there between. Heterocycle may have aromatic character or may not have aromatic character. The terms "heterocyclic group", "heterocyclic moiety", "heterocyclic", or "heterocyclo" used alone or as a suffix or prefix, refers to a radical derived from a heterocycle by removing one or more hydrogens there from. The term "heterocyclyl" used alone or as a suffix or prefix, refers a monovalent radical derived from a heterocycle by removing one hydrogen there from. The term "heteroaryl" used alone or as a suffix or prefix, refers to a heterocyclyl having aromatic character. Heterocycle includes, for example, monocyclic heterocycles such as: aziridine, oxirane, thiirane, azetidine, oxetane, thietane, pyrrolidine, pyrroline, imidazolidine, pyrazolidine, pyrazoline, dioxolane, sulfolane 2,3-dihydrofuran, 2,5-dihydrofuran tetrahydrofuran, thiophane, piperidine, 1,2,3,6-tetrahydro-pyridine, piperazine, morpholine, thiomorpholine, pyran, thiopyran, 2,3-dihydropyran, tetrahydropyran, 1,4-dihydropyridine, 1,4-dioxane, 1,3-dioxane, dioxane, homopiperidine, 2,3,4,7-tetrahydro-1H-azepine homopiperazine, 1,3-dioxepane, 4,7-dihydro-1,3-dioxepin, and hexamethylene oxide. For example, heterocycles useful in the methods of the disclosure include:

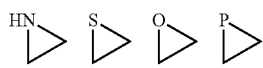

In addition, heterocycle includes aromatic heterocycles (heteroaryl groups), for example, pyridine, pyrazine, pyrimidine, pyridazine, thiophene, furan, furazan, pyrrole, imidazole, thiazole, oxazole, pyrazole, isothiazole, isoxazole, 1,2,3-triazole, tetrazole, 1,2,3-thiadiazole, 1,2,3-oxadiazole, 1,2,4-triazole, 1,2,4-thiadiazole, 1,2,4-oxadiazole, 1,3,4-triazole, 1,3,4-thiadiazole, and 1,3,4-oxadiazole.

A framework can undergo post synthetic modification by reacting the framework with a reactive species. For example, if a side group on a linking moiety comprises, for example, $NH_2$ reaction with an aziridine containing compound results in opening of the reactive species ring depicted generally by:

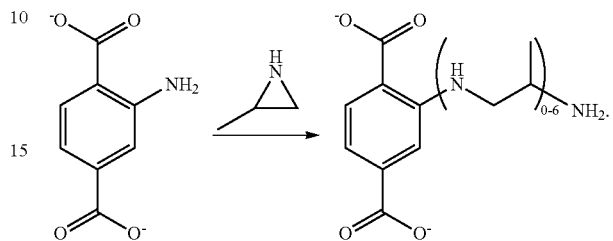

Using such methods variations and functionalized frameworks can be generated. As shown above, the reaction of the linking moiety with aziridine results in the addition of a side group to the linking moiety. In such a framework the reactive side group can extend into the pores of the framework thereby modifying their size or charge.

The preparation of the frameworks of the disclosure can be carried out in either an aqueous or non-aqueous system. The solvent may be polar or non-polar as the case may be. The solvent can comprise the templating agent or the optional ligand containing a monodentate functional group. Examples of non-aqueous solvents include n-alkanes, such as pentane, hexane, benzene, toluene, xylene, chlorobenzene, nitrobenzene, cyanobenzene, aniline, naphthalene, naphthas, n-alcohols such as methanol, ethanol, n-propanol, isopropanol, acetone, 1,3,-dichloroethane, methylene chloride, chloroform, carbon tetrachloride, tetrahydrofuran, dimethylformamide, dimethylsulfoxide, N-methylpyrolidone, dimethylacetamide, diethylformamide, thiophene, pyridine, ethanolamine, triethylamine, ethlenediamine, and the like. Those skilled in the art will be readily able to determine an appropriate solvent based on the starting reactants and the choice of solvent is not believed to be crucial in obtaining the materials of the disclosure.

Templating agents can be used in the methods of the disclosure. Templating agents employed in the disclosure are added to the reaction mixture for the purpose of occupying the pores in the resulting crystalline base frameworks. In some variations of the disclosure, space-filling agents, adsorbed chemical species and guest species increase the surface area of the metal-organic framework. Suitable space-filling agents include, for example, a component selected from the group consisting of: (i) alkyl amines and their corresponding alkyl ammonium salts, containing linear, branched, or cyclic aliphatic groups, having from 1 to 20 carbon atoms; (ii) aryl amines and their corresponding aryl ammonium salts having from 1 to 5 phenyl rings; (iii) alkyl phosphonium salts, containing linear, branched, or cyclic aliphatic groups, having from 1 to 20 carbon atoms; (iv) aryl phosphonium salts, having from 1 to 5 phenyl rings; (v) alkyl organic acids and their corresponding salts, containing linear, branched, or cyclic aliphatic groups, having from 1 to 20 carbon atoms; (vi) aryl organic acids and their corresponding salts, having from 1 to 5 phenyl rings; (vii) aliphatic alcohols, containing linear, branched, or cyclic aliphatic groups, having from 1 to 20 carbon atoms; or (viii) aryl alcohols having from 1 to 5 phenyl rings.

Crystallization can be carried out by leaving the solution at room temperature or in isothermal oven for up to 300° C.; adding a diluted base to the solution to initiate the crystallization; diffusing a diluted base into the solution to initiate the crystallization; and/or transferring the solution to a closed vessel and heating to a predetermined temperature.

The frameworks of the disclosure can be used in various devices and systems to perform the catalysis described and depicted in FIG. 3. The MOF and/or MOP compositions can be added to a reaction vessel comprising a reagents to be coupled (e.g., homocoupled). For example, a MOF-199 can be added to a reaction mixture comprising an arylboronic acid to be coupled and the reaction allowed to proceed. In some embodiments, the reaction mixture can be passed through a column comprising a MOF and/or MOP that catalyzes the homo-coupling of the reagents. In another embodiment, the reaction vessel can be agitated or mixed. As described elsewhere herein the MOF and/or MOP can be reused. In some embodiments, the reaction is carried out at room temperature. In another embodiment, the reaction is carried out with stirring at room temperature. After filtration and washing with fresh dichloromethane, the MOF can be fully recovered and re-used without any significant loss of activity.

The following examples are intended to illustrate but not limit the disclosure. While they are typical of those that might be used, other procedures known to those skilled in the art may alternatively be used.

EXAMPLES

Materials: MOF-199 (Basolite C300, Aldrich), cyclohexylamine, triethylamine, phenylbornic acid, 4-nitrophenylboronic acid, 4-cyanophenylbornic acid, 4-chlorophenylboronic acid, 4-ter-burlyphenylboronic acid, 4-(dimethylamino)-phenylboronic acid, naphthalene-1-bonronic acid and 1,3,5-trimethyoxybenzene were purchased form Aldrich Chemical Co. Dichloromethane was purchased from Fisher Scientific International Inc. All starting materials were used without further purification. All experimental operations, unless otherwise noted, were performed in air.

General Homo-coupling Reaction Procedure:

A mixture of arylboronic acid, (3.01 mmol), cyclohexylamine (0.248 g, 286 μL, 2.51 mmol) and triethylamine (0.253 g, 348 μL, 2.49 mmol) were premixed and dissolved in 20 mL dichloromethane in a 50 mL round-bottom flask. MOF (0.100 g, 0.165 mmol, 0.495 mmol Cu(II)) or cupric acetate monohydrate ($Cu(OAc)_2 \cdot H_2O$, 0.100 g, 0.501 mmol) was then added to the solution. The mixture was stirred at room temperature for 5 h, followed by filtration and washing with fresh dichloromethane. The excess dichloromethane in the filtrate was subsequently removed by rotovap. 1,3,5-trimethoxybenzene (0.168 g, 1.00 mmol) was added to the filtrate as internal standard for $^1H$ NMR. Chemical shifts of all products in $^1H$ NMR agree well with literature data.

Biphenyl: 47% yield of biphenyl (based on phenylboronic acid) was afforded when MOF was used; no biphenyl product was formed in the case of cupric acetate monohydrate. GC-MS, m/z+154.1; 4,4'-dinitrobiphenyl: 87% and 18% yields of 4,4'-dinitrobiphenyl (based on 4-nitrophenylboronic acid) were afforded when MOF and cupric acetate monohydrate were used, respectively. GC-MS, m/z+244.2; Biphenyl-4,4'-dicarbonitrile: 92% and 19% yields of biphenyl-4,4'-dicarbonitrile (based on 4-cyanophenylboronic acid) were afforded in the presence of MOF and cupric acetate monohydrate, respectively. 1.34 mmol (yield: 90%) and 1.35 mmol (yield: 92%) biphenyl-4,4'-dicarbonitrile were observed in the second and third cycles, respectively. GC-MS, m/z+204.1; 4,4'-dichlorobiphenyl: 81% and 8% yields of 4,4'-dichlorobiphenyl (based on 4-chlorophenylboronic acid) were afforded in the presence of MOF and cupric acetate monohydrate, respectively. GC-MS, m/z+223.1; 4,4'-di-tert-butylbiphenyl: 25% yield of 4,4'-di-tert-butylbiphenyl (based on 4-tert-butylphenylboronic acid) was afforded when MOF was used, but none was formed in the case of cupric acetate monohydrate. GC-MS, m/z+266.1; N,N,N',N'-tetramethyldiphenyl-4,4'-diamine: 43% and 5% yields of N,N,N',N'-tetramethyl-diphenyl-4,4'-diamine (based on 4-(dimethylamino)-phenylboronic acid) for MOF and cupric acetate monohydrate, respectively. GC-MS, m/z+240.1; 1,1'-binaphthyl: 90% and 6% yields of 1,1'-binaphthyl (based on naphthalyl-1-boronic acid) were afforded for MOF and cupric acetate monohydrate, respectively. GC-MS, m/z+254.2.

Powder X-ray diffraction (PXRD) data were collected using a Bruker D8-Discover θ-2θ diffractometer in reflectance Bragg-Brentano geometry. Cu Kα radiation (λ=1.5406 Å; 1,600 W, 40 kV, 40 mA) was focused using a planer Gobel Mirror riding the Kα line. A 0.6 mm divergence slit was used for all measurements. Diffracted radiation was detected using a Vantec line detector (Bruker AXS) (6° 2θ sampling width) equipped with a Ni monochrometer. All samples were ground to ensure mono dispersity in the bulk, and then mounted onto a glass slide fixed on a sample holder by dropping powders and then leveling the sample surface with a wide-blade spatula. The best counting statistics were achieved by using a 0.02° 2θ step scan from 1-50° with an exposure time of 0.4 s per step. The diffraction patterns collected for $Cu_3(BTC)_2$ both before and after homo-couplings are shown in FIGS. 4-10. Powder patterns of Cu3(BTC)2 after three cycles also illustrated in FIG. 11.

Figure 12:
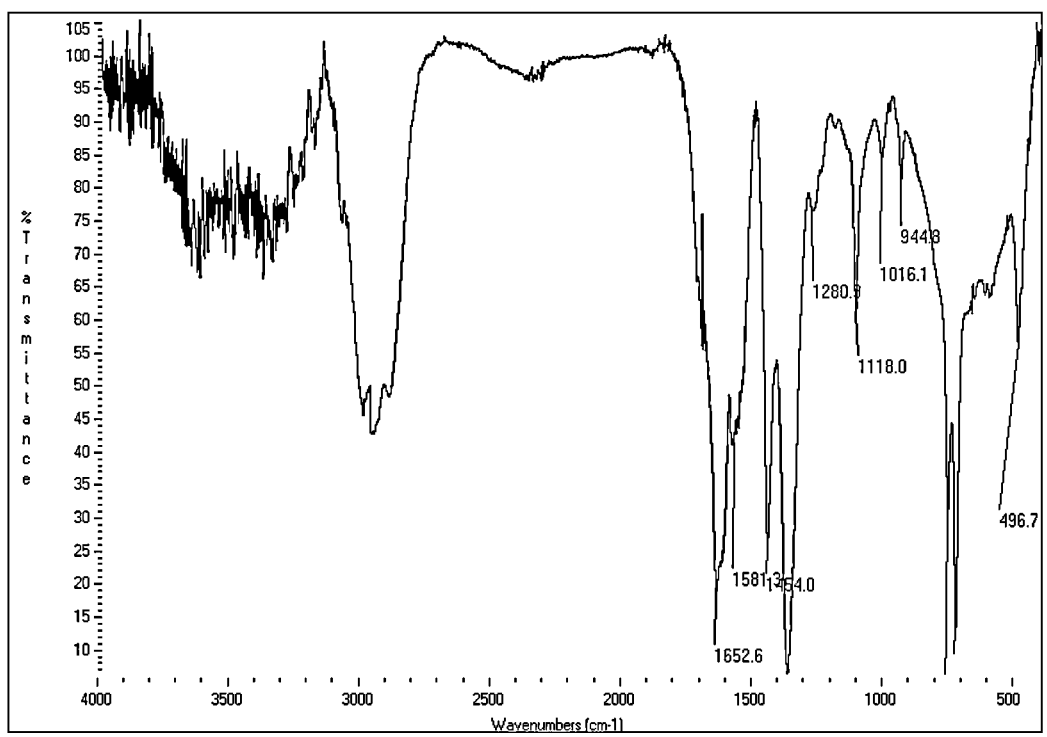
FIG. 12 shows FT-IR spectrum of fresh Cu$_3$(BTC)$_2$.
Figure 13:
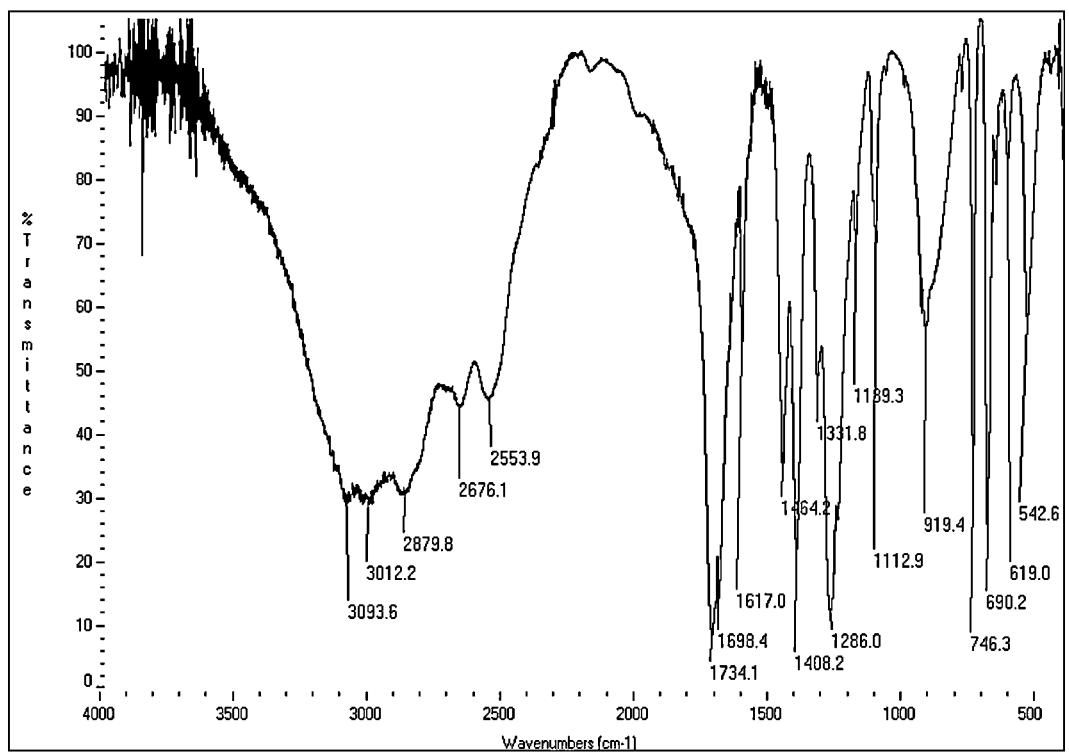
FIG. 13 shows FT-IR spectrum of benzene-1,3,5-tricarboxylic acid (BTC).
Figure 14:
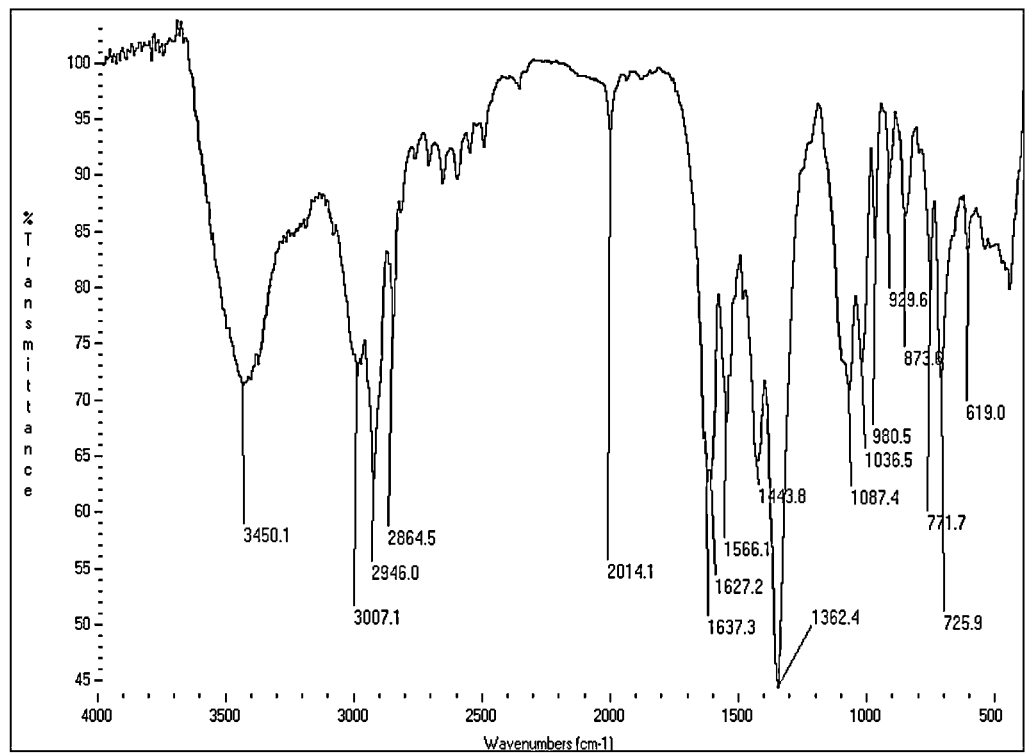
FIG. 14 shows FT-IR spectrum of recovered solid after the homo-coupling of phenylboronic acid.
Figure 15:
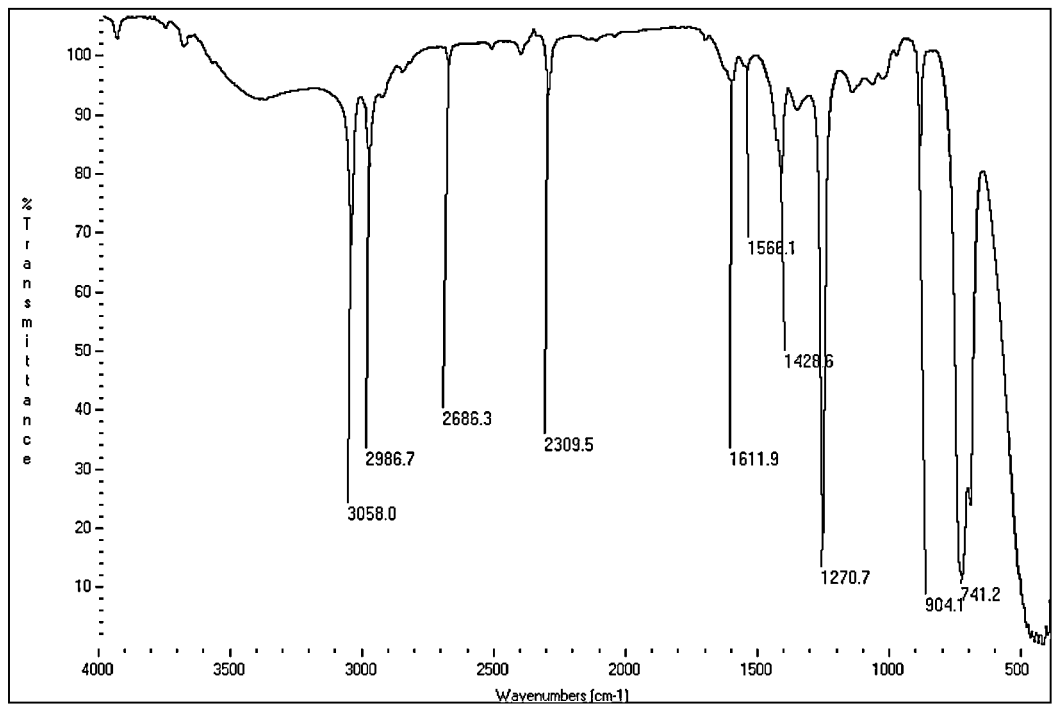
FIG. 15 shows FT-IR spectrum of recovered liquid after the homo-coupling of phenylboronic acid.

FT-IR spectra of benzyltricarboxylic acid (BTC) and $Cu_3(BTC)_2$ (fresh and after coupling reaction) were obtained as KBr pellets using Nicolet 400 Impact spectrometer. FT-IR of recovered liquid after coupling reaction was performed on two clear KBr crystal plates. As shown in FIGS. 12 and 13, the C=O stretch of carboxylates in $Cu_3(BTC)_2$ absorbs at 1653 $cm^{-1}$, whereas the C=O stretch of free carboxylic acid in BTC absorbs at 1734 $cm^{-1}$, which is a strong characteristic peak for presence of any non-coordinated carboxylic groups. Recovered $Cu_3(BTC)_2$ solid, as shown in FIG. 14, clearly indicated that no free carboxylic acid from decomposition was trapped in $Cu_3(BTC)_2$ framework. Furthermore, FIG. 15 shows that no BTC leached out into the solution. This discussion pertaining to the IR spectral relationships between these compounds is offered as support for the intactness of MOFs throughout the coupling reactions.

$^1H$ and $^{11}B$ NMR spectra were recorded at 295K on Bruke ARX 400 and ARX 500 instruments, respectively ($^1H$, 400 MHz; 11B, 160 MHz). $^1H$ chemical shift values are reported in parts per million (ppm) relative to SiMe4 (δ 0 ppm). $^{11}B$ chemical shift value are reported in ppm relative to $BF_3.Et_2O$ (δ 0 ppm). Monitor reaction by $^{11}B$ NMR: The reaction of boronic acid was monitored by $^{11}B$ NMR to track in detail of the boron source.

The $^{11}B$ NMR shift of the suspension of boronic acid in $CH_2Cl_2$ is δ 30.49 ppm, which corresponding the trimerized product boroxine $(PhBO)_3$; after 2 equivalent of cyclohexyl amine added to the solution, the solution became clear and the $^{11}B$ chemical shift showed two signals: a weak peak at δ 29.45 ppm and a strong signal of δ 19.97 ppm (we assign this to intermediate II based on the chemical shift which corresponding to a three-coordinated boron center). 5 mol % of MOF199 was added and the mixture was stirred for 1 h, followed by 11B NMR for the aliquitor. In addition to the previous two signals, a third peak at δ 3.69 ppm was observed. Although the product was not isolate this $^{11}$B chemical shift falls into a four-coordinated boron species region; hence this was tentatively assigned to a borate anion.

A number of embodiments of the invention have been described. Nevertheless, it will be understood that various modifications may be made without departing from the spirit and scope of the invention. Accordingly, other embodiments are within the scope of the following claims.

The activity of copper MOFs were tested in the homo-coupling reactions of several representative arylboronic acids with various functional groups (see Table 2A and 2B). 5.5 mol percent of MOF catalyst was added in air to a solution of dry dichloromethane containing the arylboronic acids, triethylamine and cyclohexylamine. For comparison, a nonporous cupric acetate monohydrate having the same Cu paddlewheel unit and a molecular structure was employed under identical reaction conditions. The reactions were run for 5 hours at room temperature under stirring. The homo-coupling of phenylboronic acid and tert-butyl phenylboronic acid on the MOF resulted in up to 47% yield of biaryl. In contrast, cupric acetate failed to show any observable activity. In the homo-couplings of nitro-, cyano-, chloro-, or dimethylamino-phenylboronic acids and 2-naphthylboronic acid, use of MOF catalyst gave up to 92% yield. Cupric acetate, in contrast, did catalyze these reactions with poor yields (5%-19%). The presence of MOF in catalytic quantities clearly resulted in up to 15 times higher yield.

TABLE 2A

Synthesis of biaryls with MOF catalyst and copper acetate.

| $R^3$ | $Cu_3(BTC)_2$ Yield %[2] | Biaryl Product[1] | $Cu(OAc)_2 \cdot H_2O$ Yield % |
|---|---|---|---|
| —H | 47 | biphenyl | 0 |
| —NO$_2$ | 87 | 4,4'-dinitrobiphenyl | 18 |
| —CN | 92 | 4,4'-dicyanobiphenyl | 19 |
| —Cl | 81 | 4,4'-dichlorobiphenyl | 8 |
| -t-Bu | 25 | 4,4'-di-tert-butylbiphenyl | 0 |
| —NMe$_2$ | 43 | 4,4'-bis(dimethylamino)biphenyl | 5 |
| naphthyl | 90 | 1,1'-binaphthyl | 6 |

Based on GC-MS and $^1$H NMR.

Yield of the biaryls was calculated based on recovered boronic acid. In every reaction, arylated cyclohexylamine from the Chan-Lam coupling was the only by-product.

Naphthyl-1-boronic acid was used for the last reaction.

TABLE 2B

Synthesis of biaryls with MOF catalyst and copper acetate.
Product yield and selectivity.

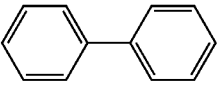 [SMILES: c1ccc(-c2ccccc2)cc1]

| | MOF-199 | | | Cu(OAc)$_2$·H$_2$O | |
|---|---|---|---|---|---|
| R | Yield %[2] | Selectivity %[3] | Product[1] | Yield % | Selectivity % |
| —H | 47 | 65 | 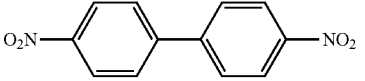 [SMILES: O=[N+]([O-])c1ccc(-c2ccc([N+](=O)[O-])cc2)cc1] | 0 | 0 |
| —NO$_2$ | 87 | 95 | 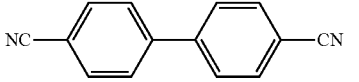 | 18 | 20 |
| —CN | 92 | 98 | 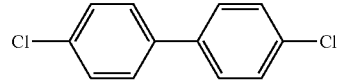 [SMILES: Clc1ccc(-c2ccc(Cl)cc2)cc1] | 19 | 24 |
| —Cl | 81 | 85 | 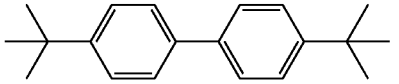 | 8 | 10 |
| -t-Bu | 25 | 74 | 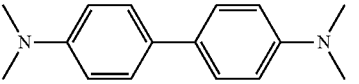 | 0 | 0 |
|  | 43 | 63 | 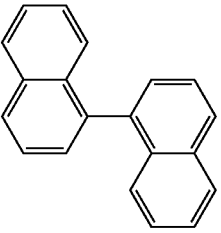 [SMILES: c1ccc2c(-c3cccc4ccccc34)cccc2c1] | 5 | 8 |
| 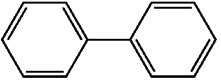 | 90 | 99 | | 6 | 24 |
| —H[4] | 65 | 75 | | 0 | 0 |

[1]Based on GC-MS and 1H-NMR.
[2]Yeild of the biaryls was calculated based on boronic acid.
[3]MOP-OH was used as the catalyst.

Figure 2:
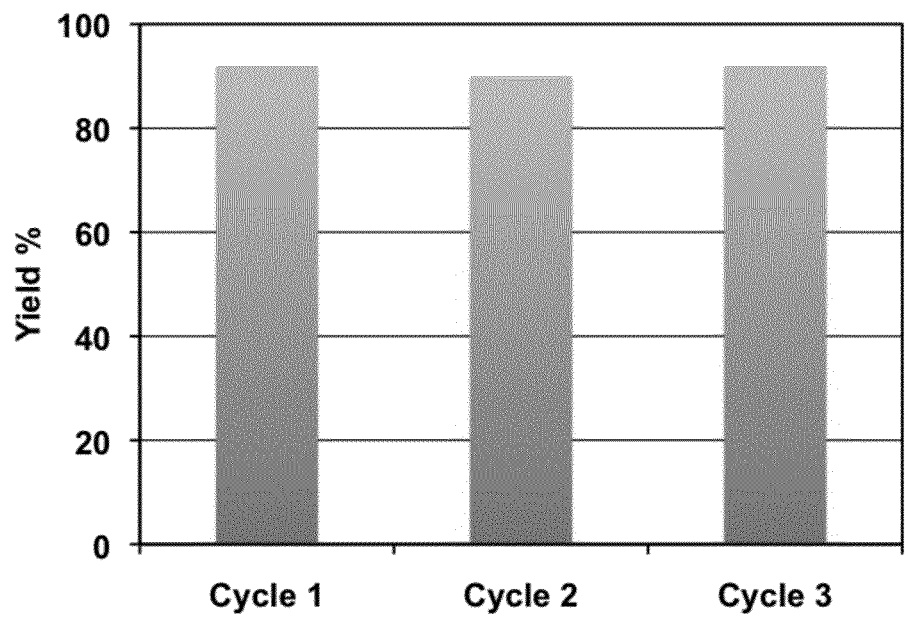
FIG. 2 shows a comparison of the yields for three cycles of the homo-coupling of 4-cyanophenylboronic acid using recycled Cu$_3$(BTC)$_2$.
Figure 11:
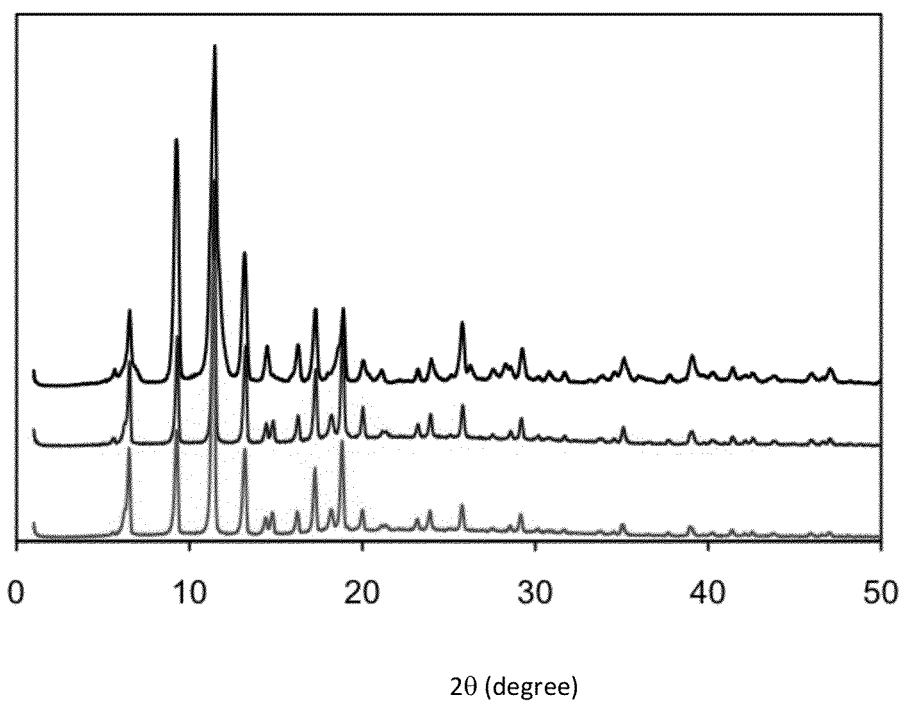
FIG. 11 shows a comparison of the experimental PXRD patterns of Cu$_3$(BTC)$_2$ after first cycle homo-coupling of 4-cyanophenylboronic acid (bottom), Cu$_3$(BTC)$_2$ after second cycle (middle), and Cu$_3$(BTC)$_2$ after third cycle (top).

After filtration and washing with fresh dichloromethane, the MOF can be fully recovered and re-used without any significant loss of activity. The PXRD pattern of MOF after each homo-coupling was measured and compared to the original. No apparent changes or shifts were observed. Furthermore, three continuous reactions were carried out for the homo-coupling of 4-cyanophenylboronic acid using MOF. FIG. 2 and FIG. 11 clearly show that the biaryl yield was maintained throughout all cycles. It is note-worthy that no further re-activation is needed between cycles, which offer great potential in industrial scale continuous production. In order to further determine whether the reactions take place under completely heterogeneous conditions, control experiments and several leaching tests were conducted. First, control experiments were performed in the absence of MOF under identical conditions, and no conversion, as monitored by GC-MS and 1H NMR, was observed for any homo-coupling. Second, no further conversion was observed when the filtrate from each reaction catalyzed by MOF was recovered and used with fresh reactants. Third, the FT-IR spectra of both recovered solids and liquids after the homo-coupling of phenylboronic acid were measured. As expected, no carbonyl stretch from free carboxylic acid was observed (FIGS. 12 and 15), which indicates that the MOF network remains intact throughout the reactions. The coupling reactions were also monitored using $^{11}$B NMR. Based on the boron species presented in the catalytic cycle and the Homo-coupling reaction mechanism.

The data demonstrate that a copper-containing MOF can serve as an alternative catalyst for precious metal-dominated oxidative homo-coupling reactions of aryl boronic acids with comparable yield. More importantly, in the search for versatile and efficient catalysts for the systematic synthesis of substituted biaryls, the heterogeneous nature of MOFs may open up new possibilities for the C—C coupling of boronic acids. This discovery also shows the great potential of MOF chemistry as it introduces complexity and functionality along with exceptional porosity. Specifically, such complexity, offered by uniquely connected active centers, can lead to behavior that is unprecedented in its molecular counterparts.

What is claimed is:

1. A method to connect aryls by homocoupling comprising contacting a porous metal organic framework (MOF) or a porous metal organic polyhedral (MOP) with boronic acid substituted aryls wherein the MOF or MOP catalyze the synthesis of a biaryl through a homo-coupling reaction, wherein the MOF or MOP comprises a plurality of linking moieties that have a substructure selected from the group consisting of $(C_1-C_{20})$alkyl, $(C_3C_{20})$cycloalky, aryl, $(C_1-C_{20})$alkylamine, arylamine, and heterocycle; and wherein the substructure has one or more covalently attached $CO_2H$ linking clusters that undergo condensation with a copper metal and wherein the MOF or the MOP comprise open copper centers that are mono-dispersed throughout the pores.

2. The method of claim 1, wherein the method further comprises cupric acetate.

3. The method of claim 1, wherein the method further comprises a solvent.

4. The method of claim 1, wherein the method further comprises a base.

5. The method of claim 4, wherein the copper center of the MOF or the MOP forms a coordinate bond with the base.

6. The method of claim 1, wherein the method further comprises an oxidant.

7. The method of claim 6, wherein the one or more oxidant is air.

8. The method of claim 1, wherein the method is performed at room temperature.

9. The method of claim 1, wherein the boronic acid substituted aryls are phenylboronic acids that can be optionally substituted at the para position.

10. The method of claim 9, wherein the boronic acid substituted aryls comprise the general structure of:

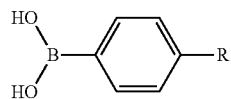

wherein,
R is selected from the group consisting of H, nitro, cyano, Cl, t-Bu, and $N(CH_3)_2$.

11. The method of claim 1, wherein the boronic acid substituted aryls is boronic acid substituted naphthalene that may or may not be further substituted.

12. The method of claim 11, wherein the boronic acid substituted naphthalene is 1-naphthylboronic acid.

13. The method of claim 1, wherein the MOF or MOP comprises one or more linking moieties comprising:

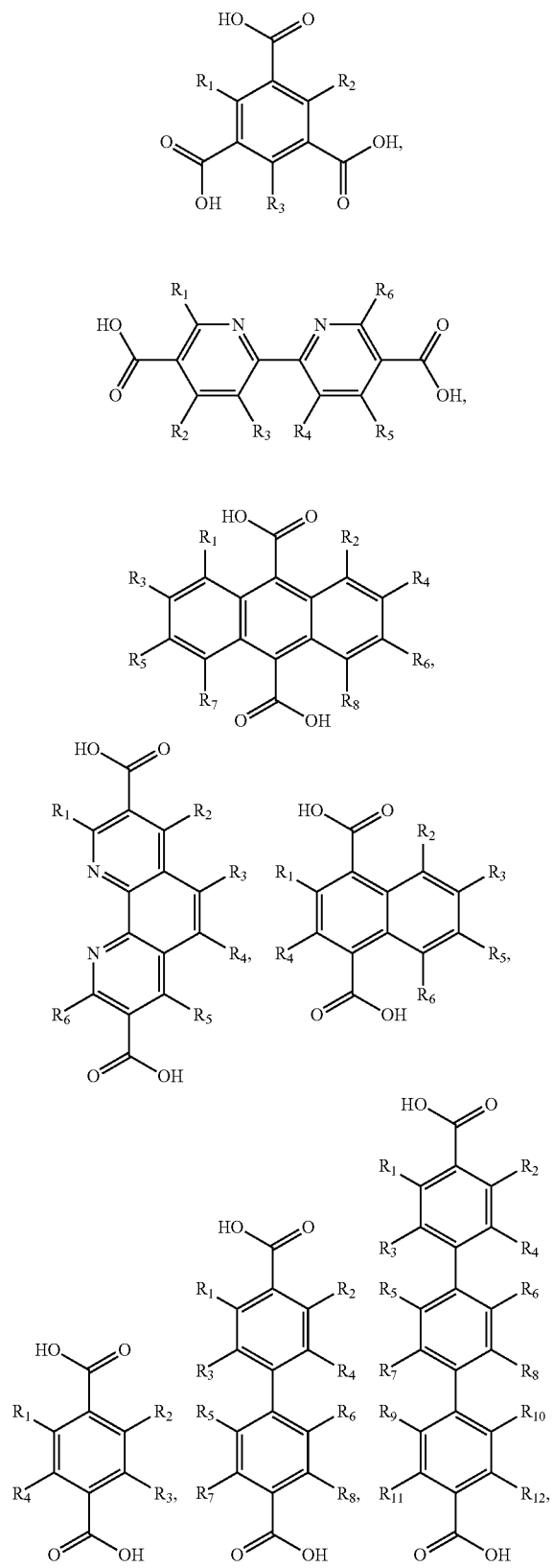

-continued

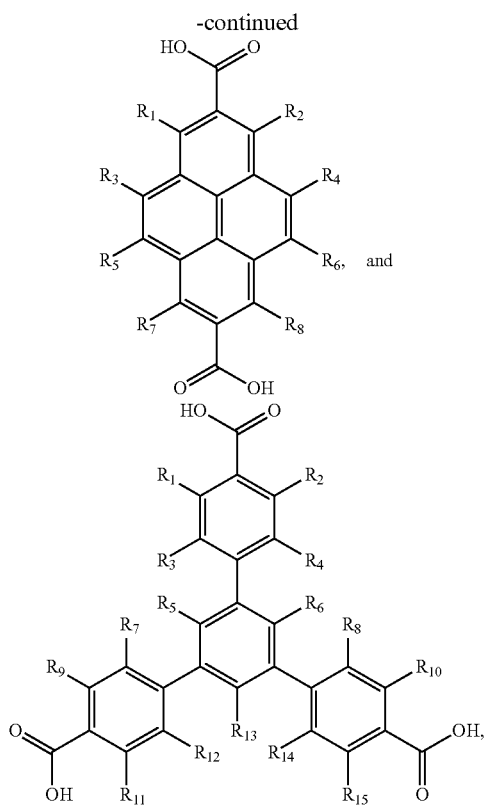

wherein,
R₁-R₁₅ are independently selected from the group consisting of H, NH₂, CN, OH, SH, P, Br, Cl, I, F,

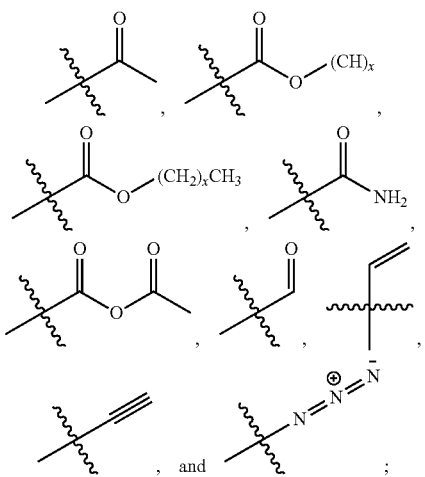

and
X is either 1, 2, or 3.

14. The method of claim 13, wherein the MOF or MOP comprises one or more linking moieties comprising:

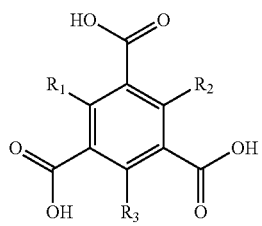

wherein,
R₁-R₃ are independently selected from the group consisting of H, NH₂, CN, OH, SH, P, Br, Cl, I, F,

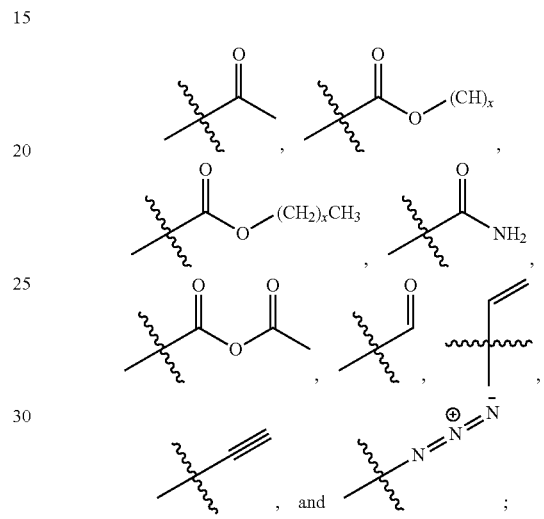

and X is either 1, 2, or 3.

15. The method of claim 14, wherein the MOF or MOP comprises one or more linking moieties comprising:

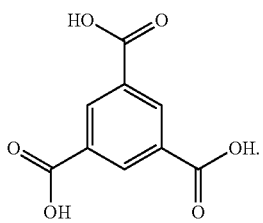 [SMILES: O=C(O)c1cc(C(=O)O)cc(C(=O)O)c1]

16. The method of claim 1, wherein the MOF or MOP contains a transition metal.

17. The method of claim 16, wherein the MOF or MOP contains Cu.

18. A method to connect aryls by homocoupling comprising contacting a metal organic framework (MOF) with boronic acid substituted aryls, wherein the MOF catalyzes the synthesis of a biaryl through a homo-coupling reaction, and wherein the MOF comprises Cu₃(BTC)₂ (where BTC is benzene-1,3,5-tricarboxylate).

19. The method of claim 1, wherein the method can be repeated for one or more cycles with the same MOF or MOP.

* * * * *